(12) United States Patent
Favre et al.

(10) Patent No.: US 12,350,332 B2
(45) Date of Patent: Jul. 8, 2025

(54) COMPOSITIONS COMPRISING SECRETORY IGA AND PROBIOTICS

(71) Applicant: SOCIETE DES PRODUITS NESTLE S.A., Vevey (CH)

(72) Inventors: Laurent Favre, Carrouge (CH); Daniel Hugelshofer, Freimettigen (CH)

(73) Assignee: Societe des Produits Nestle S.A., Vevey (CH)

( * ) Notice: Subject to any disclaimer, the term of this patent is extended or adjusted under 35 U.S.C. 154(b) by 609 days.

(21) Appl. No.: 17/597,051

(22) PCT Filed: Jun. 25, 2020

(86) PCT No.: PCT/EP2020/067906
§ 371 (c)(1),
(2) Date: Dec. 23, 2021

(87) PCT Pub. No.: WO2020/260502
PCT Pub. Date: Dec. 30, 2020

(65) Prior Publication Data
US 2022/0296706 A1     Sep. 22, 2022

(30) Foreign Application Priority Data

Jun. 28, 2019 (EP) .................................... 19183393

(51) Int. Cl.
*A61K 39/395* (2006.01)
*A61K 35/745* (2015.01)
*A61P 29/00* (2006.01)
*A61P 31/00* (2006.01)
*C07K 16/04* (2006.01)

(52) U.S. Cl.
CPC ...... *A61K 39/39508* (2013.01); *A61K 35/745* (2013.01); *A61P 29/00* (2018.01); *A61P 31/00* (2018.01); *C07K 16/04* (2013.01)

(58) Field of Classification Search
CPC . A61K 39/39508; A61K 35/745; A61P 31/00; A61P 29/00; C07K 16/04
See application file for complete search history.

(56) References Cited

U.S. PATENT DOCUMENTS

| | | | |
|---|---|---|---|
| 9,629,908 B2 * | 4/2017 | Benyacoub | .......... A61K 35/747 |
| 9,822,167 B2 * | 11/2017 | Benyacoub | ........ C07K 16/1228 |
| 10,501,530 B2 * | 12/2019 | Benyacoub | ............. A61P 29/00 |
| 2017/0281757 A1 * | 10/2017 | Benyacoub | ............. A61P 37/02 |

FOREIGN PATENT DOCUMENTS

| | | |
|---|---|---|
| EP | 2138186 | 12/2009 |
| EP | 2138187 | 12/2009 |
| EP | 2762490 | 8/2014 |
| WO | 2009139624 | 11/2009 |

OTHER PUBLICATIONS

Misra et al., "Use of Bifidobacterium Bifidum in the Manufacture of Bifidus Milk and Its Antibacterial Activity", Lait, vol. 72, Issue No. 2, 1992, pp. 213-220.
Philippes Office Action for Appl No. Jan. 2021/552934 dated Oct. 4, 2024, 6 pages.
Escuder-Vieco et al. "Effect of HTST and Holder Pasteurization on the Concentration of Immunoglobulins, Growth Factors, and Hormones in Donor Human Milk" Frontiers in Immunology, Sep. 2018, vol. 9, article 2222, 12 pages.
Chen et al., "Advances in Research on the Mechanism of Production of Intestinal Mucosal Secretory Immunoglobulin A", Journal of Xinxiang Medical College, vol. 28, Issue No. 06, Nov. 10, 2011, pp. 773-775.
Jingyi et al., "Effect of a Mixture of 6 Strains of Probiotics on Allergic Airway Inflammation in a Murine Model of Asthma and its Mechanism", Journal Shanxi Medical University, vol. 49, Issue No. 06, Jun. 12, 2018, pp. 596-601.
Office Action Received for Application No. CN202080047294.7, mailed on Jul. 8, 2023, 10 Pages of Official Copy.

* cited by examiner

*Primary Examiner* — Robert A Zeman
(74) *Attorney, Agent, or Firm* — K&L Gates LLP

(57) ABSTRACT

The present invention relates to methods for producing compositions comprising secretory IgA and one or more probiotics. In particular, the invention relates to methods for producing compositions in which the secretory IgA and one or more probiotics are associated. The invention also relates to compositions obtainable by the methods and uses of the compositions, for example in reducing or preventing a non-viral infection and/or inflammation.

9 Claims, 10 Drawing Sheets

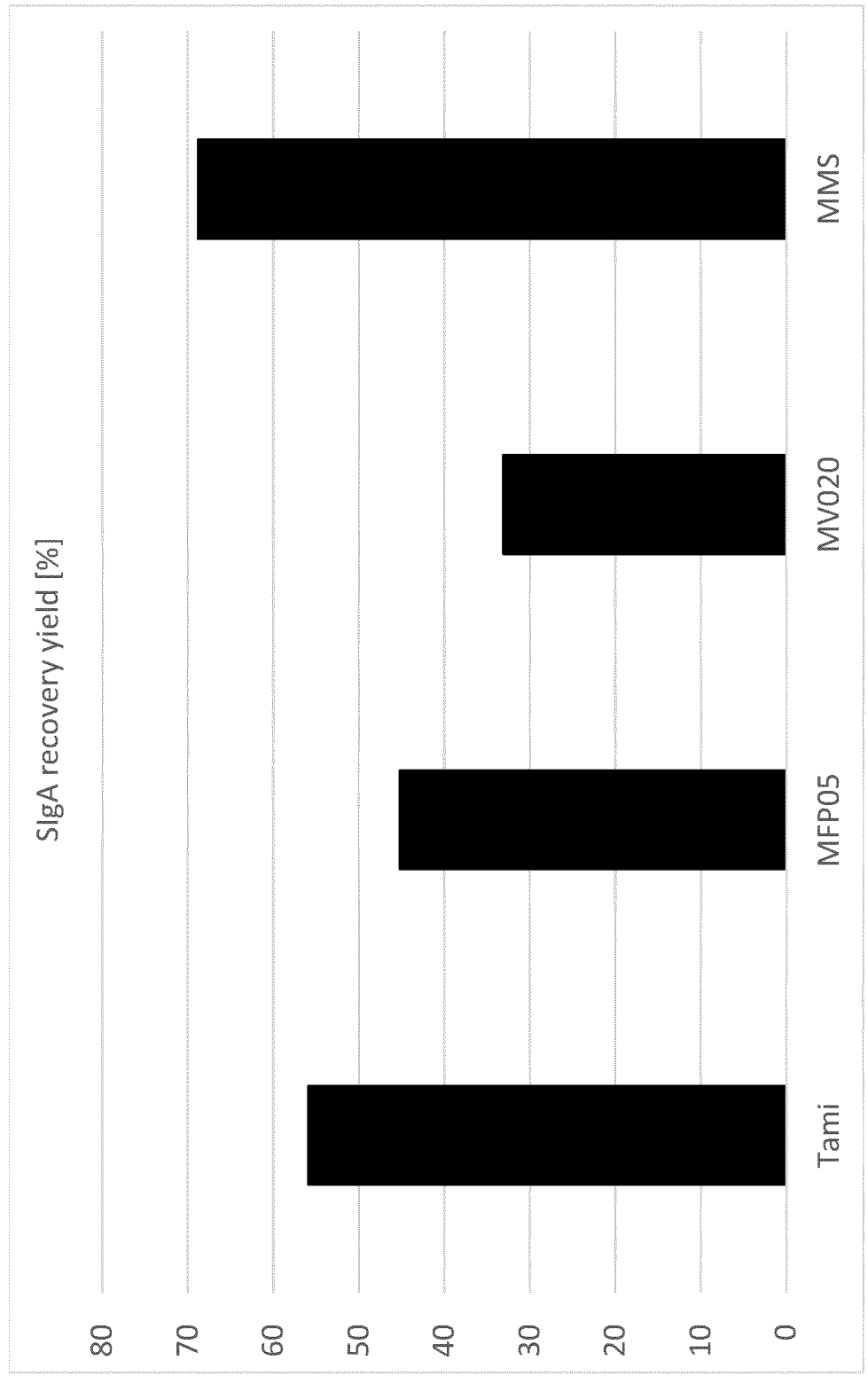

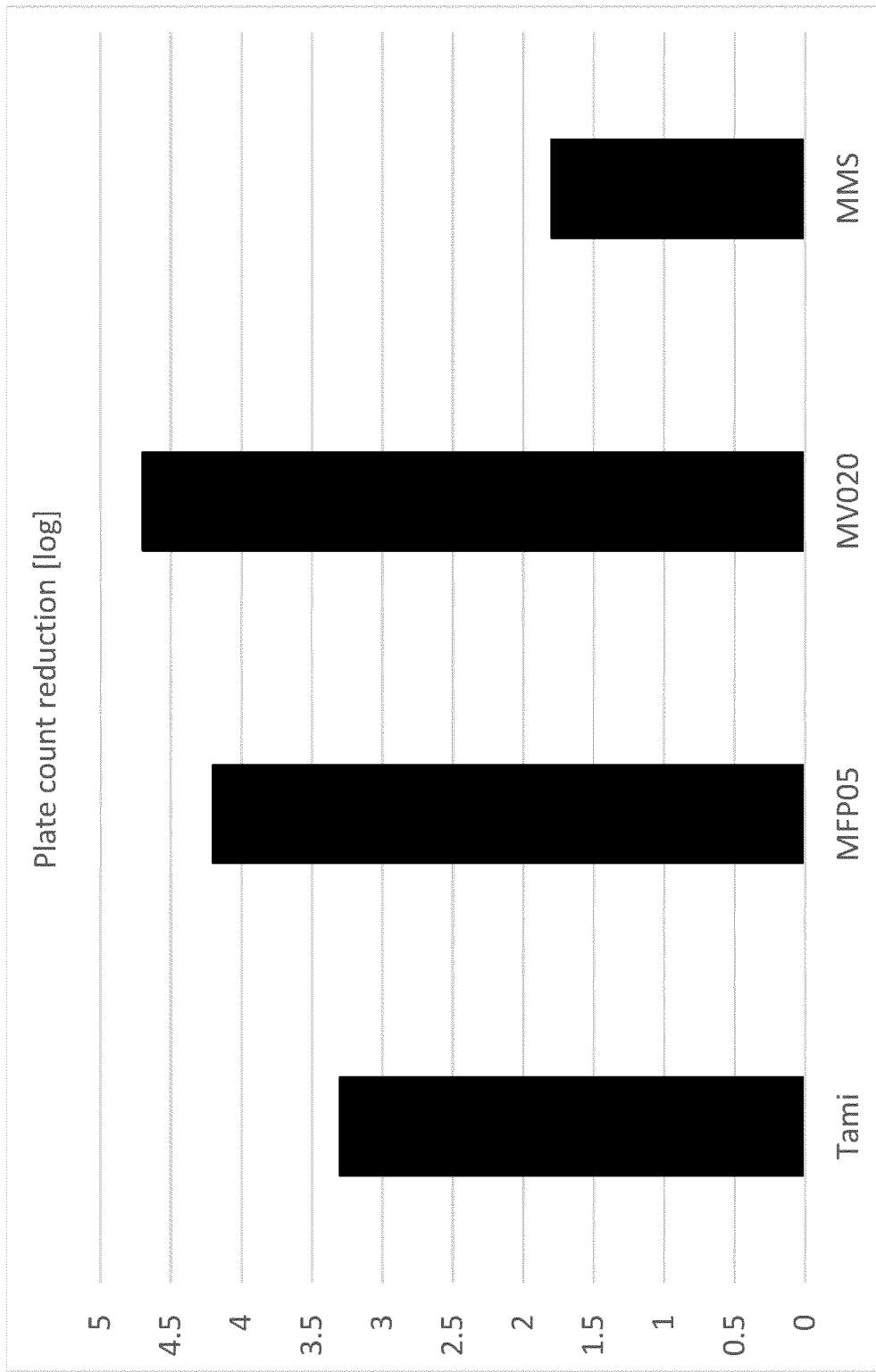

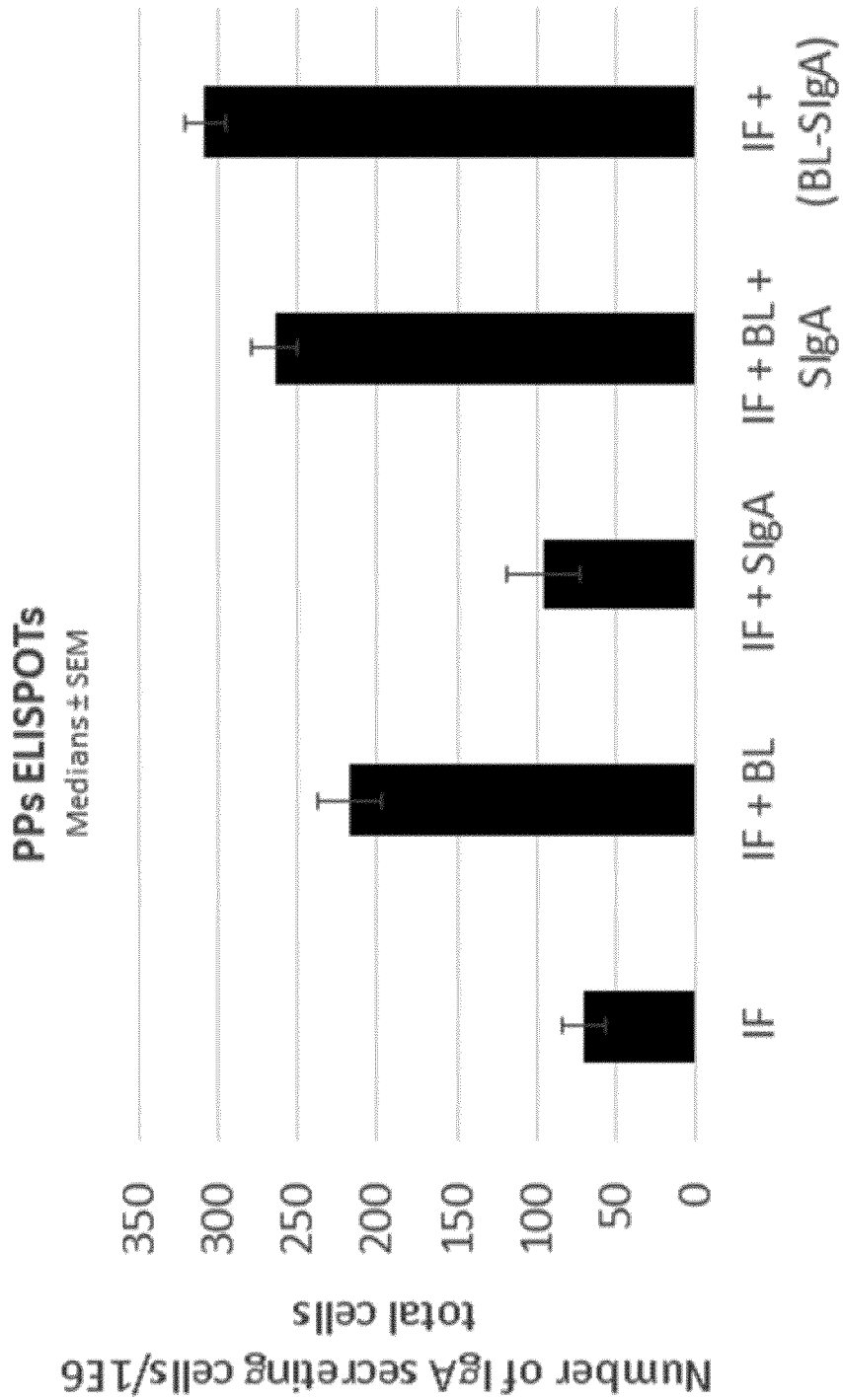

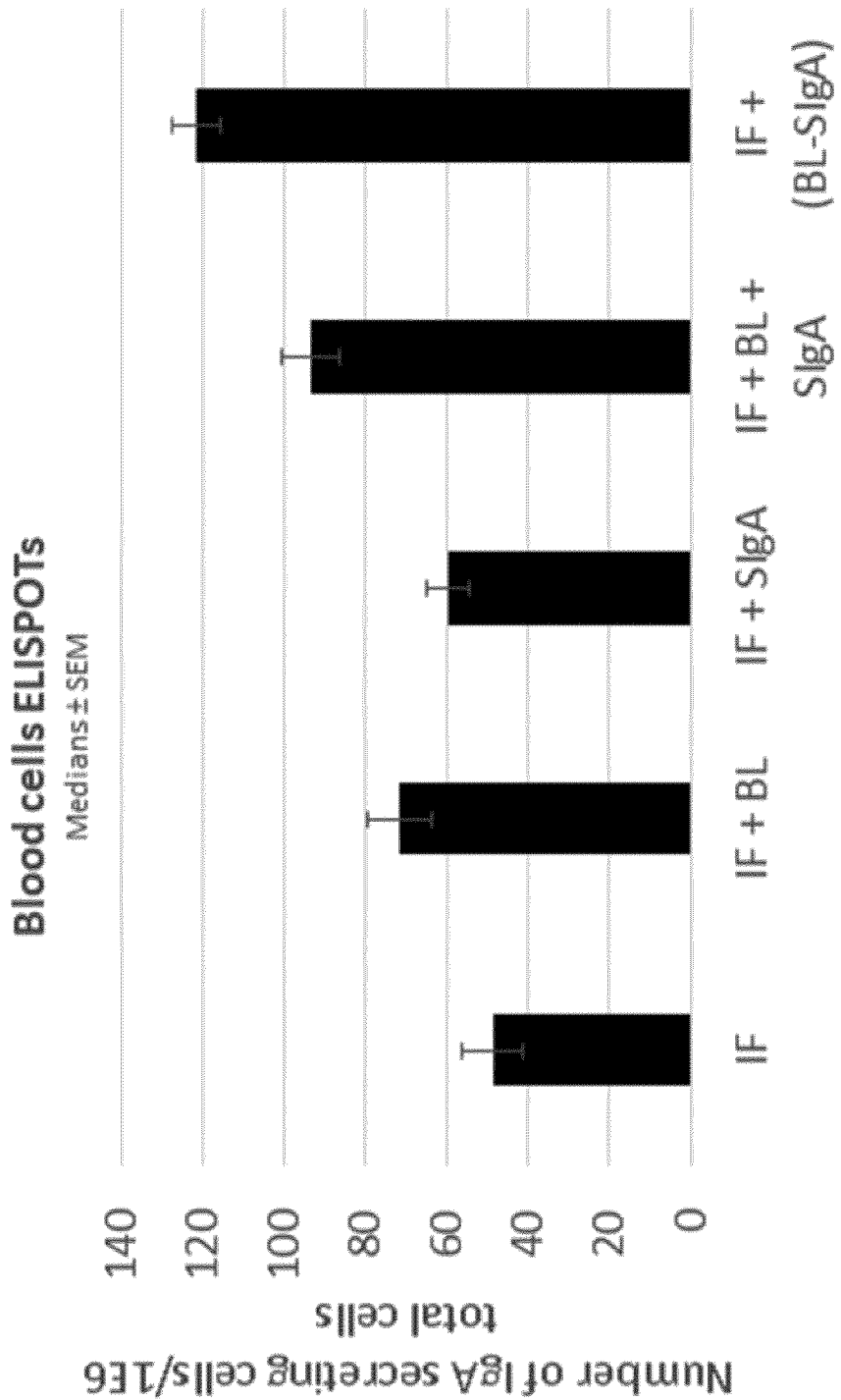

COMPOSITIONS COMPRISING SECRETORY IGA AND PROBIOTICS

CROSS REFERENCE TO RELATED APPLICATIONS

The present application is a National Stage of International Application No. PCT/EP2020/067906, filed on Jun. 25, 2020. which claims priority to European Patent Application No. 19183393.8, filed on Jun. 28, 2019, the entire contents of which are being incorporated herein by reference.

FIELD OF THE INVENTION

The present invention relates to methods for producing compositions comprising secretory IgA and one or more probiotics. In particular, the invention relates to methods for producing compositions in which the secretory IgA and one or more probiotics are associated. The invention also relates to compositions obtainable by the methods and uses of the compositions, for example in reducing or preventing a non-viral infection and/or inflammation.

BACKGROUND TO THE INVENTION

Infections are generally detrimental colonisations of a host organism by foreign species. Usually, the infecting organism attempts to utilise the host's resources to promote its own multiplication. Thereby, the infecting organism, or pathogen, may interfere with the normal functioning of the host and can lead to more infection-related disorders that may have a varying severity and that may lead in the worst case to death.

Inflammation is the complex biological response of tissues to harmful stimuli, such as pathogens, damaged cells, or irritants. It is generally a protective attempt by the organism to remove the injurious stimuli as well as to initiate the healing process for the tissue. However, non-appropriately regulated inflammation can lead to several diseases irrespective of the age of the subject.

One way to achieve the objects of preventing and treating infection and/or inflammation is to administer a composition comprising probiotics.

Probiotic microorganisms are known to have a beneficial effect on the health and well-being of the host. The use of probiotic bacteria has gained considerable attention as a safe and accessible form of prevention or treatment, for example for gastrointestinal diseases (Isolauri E, et al., Dig Dis Sci 1994, 39:2595-2600). Typical probiotic bacteria that have been employed in this respect belong to the *Lactobacillus* or the *Bifidobacterium* genus.

The effectiveness of probiotics first depends, in part, on their ability to resist to digestive tract conditions and adhere to intestinal epithelium. Further critical aspects conditioning the probiotics' potential benefit to the host are their impact on epithelium barrier function and their cross-talk with the host's mucosal immune system.

While some probiotics already achieve respectable results in terms of promoting or dampening the host immune system, it is desirable to further improve the effectiveness with which the probiotic microorganisms can interact with the host mucosa and thus beneficially impact the host.

Antibodies are often glycoproteins, which specifically recognise antigens. In vertebrates, five immunoglobulin classes are described, including IgG, IgM, IgA, IgD and IgE, all of which differ in their function in the immune system.

One of the most characteristic features of the mucosal immune system in most mammals is the dominant presence of secretory antibodies, particularly secretory IgA (SIgA), an antibody class unique to mucosae. Biosynthesis of polymeric IgA (pIgA) takes place in the mucosal lamina propria, and its transport across the epithelium lining the mucosal surfaces is ensured by the polymeric Ig receptor (pIgR) expressed at basolateral side of crypt and columnar epithelial cells. During transport of the pIgR-pIgA towards the apical cellular surface, the extracellular part of the pIgR, termed the secretory component (SC), is cleaved and remains associated with polymeric IgA, hence releasing SIgA in the mucosal lumen.

Part of the present inventors previously identified SIgA antibodies capable of associating and forming complexes with strains of commensal bacteria. In particular, it was found that SIgA antibodies, when associated with probiotics, promote the interaction and further cross-talk of probiotics with the host, which contributes to the enhancement of health benefits of probiotics such as triggering an immune boosting effect against infections or preventing any potential damaging inflammatory process (WO2009/156301 and WO2009/156307).

It is challenging to produce infant formula containing bioactive ingredients such as SIgA while adhering to current quality standards and regulatory requirements, namely in terms of microbiological contamination. Current usual processes to produce commercial infant formula powders indeed rely on high heat treatments (such as for example 145° C. for 6 s), which are totally deleterious to bioactive SIgA. Thus, it is desirable to provide a process that would enable to obtain SIgA having the required level of sterility for infant nutrition, while keeping its bioactivity and thus capacity to promote health benefits of probiotics post association to them. Also it is desirable to optimize the manufacturing process of nutritional compositions comprising bioactive SIgA associated with probiotics. Indeed SIgA is not present in existing infant formulas (IF) due to the heating steps involved in manufacturing the infant formulas.

There is also a need to improve conditions of SIgA and probiotic association to form the complexes, in particular to obtain complexes having optimized bioactivity. Indeed, the complexity of the matrix environment and temperature can have a strong impact on the dynamics of probiotics and SIgA association and thus efficiency of the complexes.

SUMMARY OF THE INVENTION

The inventors have developed an improved method for the production of compositions comprising bioactive SIgA and one or more probiotics, in particular a method that leads to optimized association of the SIgA and the probiotic. Such method leads to compositions containing probiotic-SIgA complexes with optimized bioactivity to promote health benefits and with a microbiological safety suitable for use in products for sensitive consumers, such as infant formula.

In one aspect, the invention provides a method for production of a composition comprising secretory IgA and a probiotic, the method comprising the steps of:
  (a) providing a source of SIgA in the form of milk or a fraction thereof;
  (b) optionally microfiltering the milk;
  (c) pasteurising the milk at a temperature of 61-200° C.;
  (d) optionally spray-drying at a liquid concentrate temperature of less than 70° C.;

(e) admixing with the probiotic, wherein the admixing is carried out at a temperature of 1-45° C. for a duration of 10-1440 min; and (f) optionally spray-drying at a liquid concentrate temperature of less than 70° C.

In another aspect, the present invention provides a composition obtainable or obtained using the method of the present invention.

In yet a further aspect the invention relates to compositions obtainable or obtained using the process of the present invention, for use in modulating, reducing, preventing and/or treating infections and/or inflammation.

In another embodiment, the present invention provides a product comprising a composition obtained by the process of the present invention.

Figure 1:
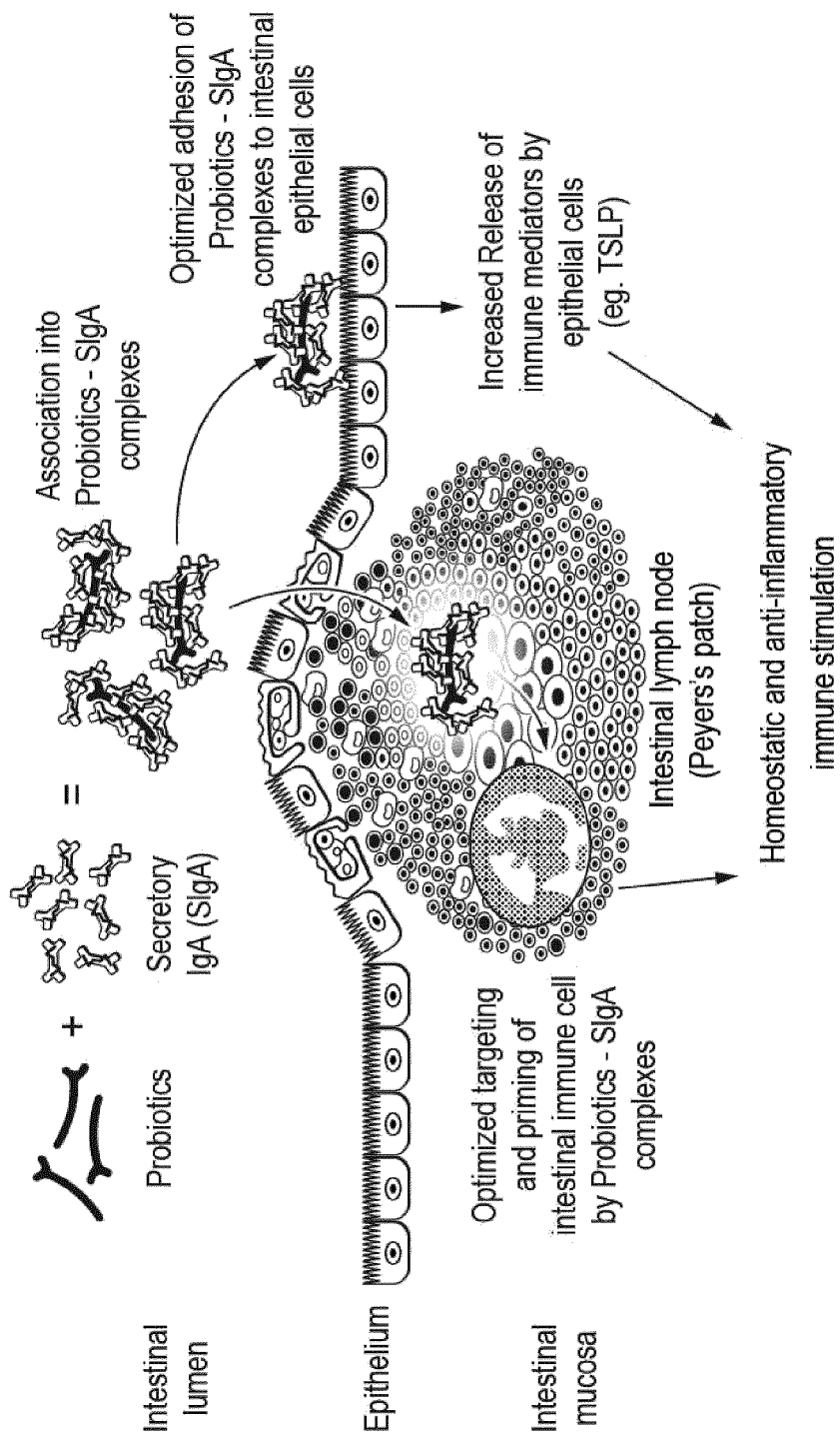
FIG. 1

A schematic representation of the putative mechanism leading to improvement of the effects of probiotics by SIgA, when associated with them, by increasing the interaction with the intestinal mucosa of the host. Depicted are possible and documented routes of interaction of SIgA associated with commensal bacteria with the host intestinal mucosa.

FIG. 2

Results of the validation trial designed to check the ability of the TSLP excretion bioassay to assess improvement of probiotics efficacy upon association with SIgA, as referred to in the introductory part of the examples section. Compared to plain epithelial cells (without probiotics), addition of probiotics alone stimulates production of Thymic Stromal LymphoPoietin (TSLP) by epithelial cells. Association of increasing quantities of purified intact SIgA to the same quantity of probiotics increases TSLP production by epithelial cells in a dose-dependent manner.

FIG. 3

Results of SIgA yield as determined by ELISA (FIG. 3A) and microbial load log reduction (FIG. 3B) in milk after microfiltration with diverse membranes at a temperature between 52 and 55° C., as described in Example 2.

FIG. 4

Results of semi-quantitative ELISA and TSLP excretion bioassay quantitations in milk after heat treatment under diverse conditions of time and temperature, as described in Example 3, allowing relative comparison between the ELISA and bioactivity quantitations of the different samples, as compared to un-treated RO milk (Reference).

FIG. 5

Results of TSLP excretion bioassay after performing the association step by incubating RO skimmed milk and BL818 mixtures under various conditions of time and temperature as described in Example 4, compared to BL alone (BL818 not associated with SIgA) and a plain cells control, where neither BL nor SIgA are added to the bioassay.

FIG. 6

Results of TSLP excretion bioassays after performing the association step with various BL818 concentrations as described in Example 5.

FIG. 7

Results of TSLP excretion bioassays of complexes formed between SIgA and either liquid or spray-dried biomass, as described in Example 6.

FIG. 8

ELISPOTs measurements allowing assessment of the impact on immune maturation at both mucosal (PPs; FIG. 8A) and systemic (blood; FIG. 8B) levels of early life supplementation with different Infant Formula prototypes containing probiotics alone, SIgA alone or combination of both, as described in Example 7.

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Process

The invention provides a method for production of a composition comprising SIgA and a probiotic, the method comprising the steps:

(a) providing a source of SIgA in the form of milk or a fraction thereof;

(b) optionally microfiltering the milk;

(c) pasteurising the milk at a temperature of 61-200° C.;

(d) optionally spray-drying at a liquid concentrate temperature of less than 70° C.;

(e) admixing with the probiotic, wherein the admixing is carried out at a temperature of 10-45° C. for a duration of 10-1440 min; and (f) optionally spray-drying at a liquid concentrate temperature of less than 70° C.

Providing a Source of SIgA

Immunoglobulin A (IgA) is an antibody, which plays an important role in the immune function of mucous membranes. IgA may be classified as serum IgA or secretory IgA.

Secretory IgA (SIgA), which is the predominant and more stable immunoglobulin in intestinal mucosal secretions, was found to be particularly effective for the present purpose.

Secretory IgA may be constituted of 2-4 IgA monomers that may be linked by two additional chains. One of the additional chains, termed the J (joining) chain is rich in cysteine and structurally distinct from other immunoglobulin chains, and is formed in the IgA-secreting cells.

Preferably, the secretory IgA is bioactive secretory IgA (i.e. secretory IgA that is able to carry out its natural functions, such as binding to epitopes; for example the bioactive secretory IgA is not denatured).

The source of SIgA is in the form of milk or a milk fraction. In some embodiments, the milk is cow's milk, sheep's milk, goat's milk, human milk, horse milk or camel milk. In preferred embodiments, the milk is cow's milk. In a preferred embodiment, the milk is skimmed milk. In some embodiments, the milk is colostrum. In some embodiments, the milk fraction is whey.

In an embodiment, the milk used as the source of SIgA is concentrated milk. In a preferred embodiment, the milk is first skimmed by centrifugation and then concentrated by reverse osmosis.

In some embodiments, the milk provided in step (a) has not been exposed to a temperature of greater than 70° C., preferably 58° C., following expression. In preferred embodiments, the milk provided in step (a) has not been exposed to a temperature of greater than 15° C. following expression. In an embodiment, the milk or milk fraction used as a source of SIgA has not been pasteurized.

In some embodiments, the milk provided in step (a) comprises 9-30%, preferably 18-26%, total solids.

In some embodiments, the mixture of step (e) comprises 15-50% total solids.

Microfiltration

Microfiltration (MF) is a physical separation process where a starting liquid is passed through a membrane with particular pore sizes to separate microorganisms and suspended particles from process liquid.

Microfiltration is commonly used in the dairy industry, particularly for milk and whey processing. For example, microfiltration aids the removal of bacteria and spores from milk.

Microfiltration allows for an extended shelf-life of product. In addition, microfiltration may be used to separate casein from whey proteins. This results in a casein-rich concentrate that may be used for cheese making, and a whey/serum protein stream which may be further processed to make whey protein concentrate.

Processes for microfiltration are well known in the art. For example, microfiltration may be carried out using polymeric membrane or ceramic membranes.

The present inventors have identified that the size of the pores of the microfiltration membrane had an impact on the retention of SIgA in the composition. Small pore sizes provide the highest reduction of microbial contamination but lead to the largest loss of SIgA, while larger pores are less efficient in reducing the microbial contamination but lead to larger amounts of SIgA in the composition. It is thus preferred to use a pore size that provides good balance between microbial contamination reduction and retention of SIgA, leading to a composition that has a microbial content that makes it suitable for use in sensitive products, such as for example infant formula and having sufficient amounts of SIgA. Thus preferably, membranes are used that have a pore size of greater than 500 nm, preferably 1000 to 1400 nm.

In some embodiments, the microfiltration step (b) is carried out at a temperature of 10-70° C. In preferred embodiments, the microfiltration of step (b) is carried out at a temperature of 10-62° C.

In cases wherein the milk or milk fraction is concentrated, such as for example by reverse osmosis (RO), the microfiltration step can be performed before or after the concentration step. In embodiments wherein whole milk is used a source of SIgA, skimmed by centrifugation and concentrated, the microfiltration step can be carried out before or after the concentration step (such as RO), preferably after the concentration step (such as RO).

Pasteurization

Pasteurization is a commonly used process in which products such as foods (e.g. milk and fruit juice) are heat treated to eliminate pathogens. The process is generally intended to make foods safer by destroying or inactivating organisms that can be pathogen or otherwise contribute to spoilage, including vegetative bacteria but not bacterial spores.

Pasteurisation is used widely in the dairy industry and other food processing industries to achieve food preservation and food safety.

Differing methods for carrying out pasteurisation are well known in the art and include the use of indirect heat exchangers and direct steam injection (DSI).

In some embodiments, the pasteurising of step (c) is carried out at a temperature of 61-120° C. for a duration of 0.1-200 s. In preferred embodiments, the pasteurising of step (c) is carried out at a temperature of 70-90° C. for 2-70 s, preferably 75-85° C. for 5-15 s. In preferred embodiments, the pasteurising of step (c) is carried out at a temperature of 82-84° C. for 5-7 s.

In other embodiments, the pasteurising of step (c) is carried out at a temperature of 120-200° C.

In some embodiments, the pasteurising of step (c) is carried out at a temperature of 120-200° C. for a duration of 0.3-2 s.

Spray-Drying

Spray-drying is a commonly used method for producing a dry powder from a liquid or slurry by rapidly drying with a hot gas, and is regularly used for drying thermally-sensitive materials such as foods and pharmaceuticals. Air may be used as the heated drying medium; although inert gases such as nitrogen may also be used. Spray dryers generally disperse the liquid or slurry using an atomiser or spray nozzle to produce a controlled drop size spray.

Spray-drying is used widely in the food and pharmaceutical industries, and equipment suitable for carrying out spray-drying is widely available.

In preferred embodiments, the spray-drying of step (d) and/or step (f) is carried out at a liquid concentrate temperature of less than 15° C.

In some embodiments, the spray-drying of step (d) and/or step (f) is carried out with an exhaust air temperature of 40-90° C.

Association of Probiotics and SIgA

In some embodiments, the admixing of step (e) is carried out at a temperature of 12-45° C., preferably 15-45° C. for a duration of 10-360 min, preferably for a duration of 10-200 min.

In some embodiments, the admixing of step (e) is carried out at a temperature of 30-38° C., preferably 36-38° C.

In some embodiments, the admixing of step (e) is carried out for a duration of 25-60 min, preferably 25-40 min, more preferably 28-32 min.

In preferred embodiments, the admixing of step (e) is carried out at a temperature of 36-38° C. for a duration of 28-32 min.

All probiotic microorganisms may be used in accordance with the invention. As used herein, the term "probiotic" means microbial cells and preparations, or components of microbial cells, with a beneficial effect on the health or well-being of the host (Salminen S, Ouwehand A. Benno Y. et al "Probiotics: how should they be defined" Trends Food Sci. Technol. 1999:10 107-10).

In some embodiments, the probiotic is selected from the group consisting of *Bifidobacterium, Lactobacillus, Streptococcus* and *Saccharomyces*, or comprises a combination thereof.

In some embodiments, the probiotic is selected from the group consisting of *Bifidobacterium longum, Bifidobacterium lactis, Lactobacillus acidophilus, Lactobacillus rhamnosus, Lactobacillus paracasei, Lactobacillus johnsonii, Lactobacillus plantarum, Lactobacillus salivarius, Enterococcus faecium, Saccharomyces boulardii* and *Lactobacillus reuteri*, or comprises a combination thereof.

In preferred embodiments, the probiotic is selected from the group consisting of *Lactobacillus johnsonii* (NCC533;

CNCM I-1225), *Bifidobacterium longum* (NCC490; CNCM I-2170), *Bifidobacterium longum* (NCC2705; CNCM I-2618), *Bifidobacterium lactis* (2818; CNCM I-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724) and *Enterococcus faecium* SF 68 (NCIMB10415), or comprises a combination thereof.

In preferred embodiments, the probiotic is a *Bifidobacterium longum*, preferably *Bifidobacterium longum* subsp. *infantis*. In other preferred embodiments, the probiotic is *Bifidobacterium lactis*, preferably *Bifidobacterium lactis* CNCM I-3446.

The combination of probiotics and SIgA is particularly effective if the SIgA and probiotics are combined in complexes prior to administration. This has the advantage that the beneficial complexes do not need to form after consumption of the product, but that they are already present in the product. The methods of production of the invention promote optimal complex formation.

In some embodiments, the SIgA and at least one probiotic are associated in the composition. Preferably they are associated in the form of a complex. In such a complex or association, the SIgA is bound to the probiotic bacteria.

In some embodiments, the amount of SIgA per 2E7 CFU of the probiotic in the mixture of step (e) is 0.34 ng to 20 µg. In preferred embodiments, the amount of SIgA per 2E7 CFU of the probiotic in the mixture of step (e) is 3.4 ng to 10 µg, preferably 34 ng to 5 µg, more preferably 340 ng to 2 µg. In a preferred aspect, such amounts of SIgA refer to bioactive SIgA. Preferably, bioactive SIgA is defined as SIgA increasing probiotic-induced TSLP production, after association with the probiotics, to a level above the production induced by probiotics alone, as measured using the bioassay described in the present examples.

In some embodiments, the concentration of the probiotic in the mixture of step (e) is 1E6-1E11 CFU/mL. In preferred embodiments, the concentration of the probiotic in the mixture of step (e) is 1E8-1E10 CFU/mL.

Specific Aspect of the Process

In preferred embodiments, the method comprises the steps:
(a) providing a source of SIgA in the form of milk or a fraction thereof;
(b) optionally microfiltering the milk at a temperature of 10-65° C.;
(c) pasteurising the milk at a temperature of 82-84° C. for a duration of 5-7 s;
(d) optionally spray-drying at a liquid concentrate temperature of less than 15° C.;
(e) admixing with the probiotic, wherein the admixing is carried out at a temperature of 36-38° C. for a duration of 28-32 min; and
(f) optionally spray-drying at a liquid concentrate temperature of less than 15° C.

Composition

The present invention provides a composition obtained or obtainable by the process of the present invention, as described above.

The invention also relates to a composition comprising SIgA and at least one probiotic microorganism. The SIgA and the probiotic microorganism may preferably be combined in the composition. SIgA and the probiotic microorganism may preferably be present in a number ratio (number of SIgA molecules per CFU of bacteria) of at least 10:1, preferably at least 100:1, most preferably at least 2000:1 to 100000:1. The more SIgA molecules are attached to the surface of the probiotic microorganism the more effective the combination will be. The upper limit of SIgA saturation is determined by the surface of the probiotic microorganism and by the number of available binding sites for SIgA.

In preferred embodiments, the SIgA and the probiotic are at least partially associated in the composition.

In some embodiments, the infant formula comprises a probiotic:secretory IgA complex.

In some embodiments, the composition complies with the rules applicable to infant formula, such as those described by FAO in Annexes I and/or II of the Code of hygienic practice for powdered formulae for infants and young children CAC/RCP 66-2008. This result is achieved in particular as a result of the pasteurization step, optionally preceded by microfiltration.

Product

In an embodiment, the invention provides a product comprising a composition obtained by the process of the present invention, as described above. The composition produced by the method of the invention may be a food product, an animal feed product or a pharmaceutical composition. For example, the product may be a nutritional composition, a nutraceutical, a drink, a nutritional supplement, a fortifier or a medicament.

In some embodiments, the composition is a nutritional composition or a pharmaceutical composition.

In a preferred embodiment the food product is selected from an infant formula, a follow-up or follow-on formula, a growing-up milk, an infant cereal product, a baby food, a supplement or a fortifier.

In some embodiments, the composition is for consumption by humans or non-human animals, preferably the composition is for consumption by humans.

In some embodiments, the composition is for consumption by infants, juveniles, adults or the elderly.

Neonates, in which endogenous SIgA antibodies are barely detectable, depend on maternal IgG transferred through the placenta, and an exogenous supply of SIgA abundantly found in breast milk. Together, this confers passive immunisation in the gut, which is essential to the protection of the host during the phase of shaping and maturation of the gastrointestinal immune system In an embodiment, the composition of the present invention is for consumption by newborns and infants (up to 2 years old), preferably by non breast-fed newborns and infants (up to two years old). Indeed, the highest health benefit value of the administration of compositions comprising optimized probiotic-SIgA complexes is in situations where natural SIgA is absent or present in limited quantities. This is for example the case of non-breast fed newborns and infants up to two years old.

In preferred embodiments, the composition is an infant formula, a nutritional supplement for infants or a milk fortifier.

A nutritional supplement or a medicament may be in the form of tablets, capsules, pastilles or a liquid for example. Nutritional supplements or medicaments are preferably provided as sustained release formulations, allowing a constant supply of SIgA and probiotics for prolonged times.

The composition is preferably selected from the group consisting of milk-powder based products; instant drinks; ready-to-drink formulations; nutritional powders; nutritional liquids; milk-based products, in particular yoghurts or ice cream; cereal products; beverages; water; coffee; cappuccino; malt drinks; chocolate flavoured drinks; culinary products; soups; tablets; and/or syrups.

The composition may further contain protective hydrocolloids (such as gums, proteins, modified starches), binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials.

The composition may also contain conventional pharmaceutical additives and adjuvants, excipients and diluents, including, but not limited to, water, gelatine of any origin, vegetable gums, lignin sulfonate, talc, sugars, starch, gum arabic, vegetable oils, polyalkylene glycols, flavouring agents, preservatives, stabilisers, emulsifying agents, buffers, lubricants, colourants, wetting agents, fillers, and the like.

Further, the composition may contain an organic or inorganic carrier material suitable for oral or enteral administration as well as vitamins, mineral trace elements and other micronutrients in accordance with the recommendations of government bodies such as the USRDA.

The composition of the invention may contain a protein source, a carbohydrate source and/or a lipid source.

Any suitable dietary protein may be used, for example animal proteins (such as milk proteins, meat proteins and egg proteins); vegetable proteins (such as soy protein, wheat protein, rice protein and pea protein); mixtures of free amino acids; or combinations thereof. Milk proteins such as casein and whey, and soy proteins are particularly preferred.

If the composition includes a fat source, the fat source preferably provides 5% to 40% of the energy of the formula; for example 20% to 30% of the energy. DHA may be added. A suitable fat profile may be obtained using a blend of canola oil, corn oil and high-oleic acid sunflower oil.

A source of carbohydrates may more preferably provide between 40% to 80% of the energy of the composition. Any suitable carbohydrate may be used, for example sucrose, lactose, glucose, fructose, corn syrup solids, maltodextrins and mixtures thereof.

The composition may also contain prebiotics. The addition of prebiotics is beneficial as it can, when combined with probiotics, deliver synergistic effects in terms of the health benefits. A composition comprising a combination of prebiotics and probiotics is commonly known as a symbiotic composition.

As used herein, the term "prebiotic" means food substances that promote the growth of beneficial bacteria such as bifidobacteria or lactobacilli, and/or probiotics in the intestines. Prebiotics are not broken down in the stomach or absorbed in the GI tract of the person ingesting them, but they are fermented by the gastrointestinal microflora and/or by probiotics.

The prebiotics that may be used in accordance with the invention are not particularly limited and include all food substances that promote the growth of probiotics in the intestine. Preferably, the prebiotic is selected from the group consisting of oligosaccharides, optionally containing fructose, galactose, mannose; dietary fibres, in particular soluble fibres, soy fibres; inulin; or mixtures thereof. Preferred prebiotics are human milk oligosaccharides (HMO), bovine milk oligosaccharide (BMO), fructo-oligosaccharides (FOS), galacto-oligosaccharides (GOS), isomalto-oligosaccharides, xylo-oligosaccharides, oligosaccharides of soy, glycosylsucrose (GS), lactosucrose (LS), lactulose (LA), palatinose-oligosaccharides (PAO), malto-oligosaccharides, pectins and/or hydrolysates thereof.

The composition may also contain at least one other kind of other food grade bacteria, preferably selected from the group consisting of lactic acid bacteria, bifidobacteria, enterococci or mixtures thereof. These other food grade bacteria may contribute to obtain a healthy gut microflora and will hence contribute to achieve the object of the invention even more effectively.

The amount of SIgA required to achieve an effect is not limited. It is generally preferred if the product comprises between 0.0001 mg SIgA and 100 mg SIgA, for example between 0.0001 mg SIgA and 10 mg SIgA, per daily dose. In preferred embodiments, the composition comprises 0.001-0.1 mg secretory IgA per daily dose.

Typically, the probiotics will be effective in a large range of amounts. In some embodiments, the composition comprises between 1E2 and 1E12, preferably between 1E2 and 1E10 cells of probiotics per daily dose.

In preferred embodiments, the product is an ingestible infant composition.

As used herein, the term "ingestible infant composition" means a composition suitable for consumption by an infant. Examples of ingestible infant compositions include, but are not limited to, infant supplements and infant formulas.

During the first four months of age, infants are usually unable to consume solid foods. Accordingly, in preferred embodiments, the ingestible infant composition may be provided and/or ingested in a liquid format. In some embodiments the ingestible infant composition is for use in infants who are not able to eat solid food.

In preferred embodiments, the ingestible infant composition is an infant nutritional supplement. The supplement may be provided in addition to breast milk and/or infant formula. Thus, in preferred embodiments the ingestible infant composition is an infant supplement suitable for ingestion by infants from 0-12 months, 6 weeks to 12 months, 0-6 months, 6 weeks to 6 months, 4-6 months, preferably 0-4 months or 6 weeks to 4 months of age.

The infant supplement may further comprise one or more of the following: protein; fat (lipids); carbohydrates; and essential vitamins and minerals. The infant supplement may further comprise sweetening, flavouring and/or colouring agents.

In other embodiments, the ingestible infant composition does not comprise additional protein; fat; carbohydrates; and/or essential vitamins and minerals.

In other embodiments, the ingestible infant composition is an infant formula or follow-on formula. The term "infant formula" means a foodstuff intended for use by infants during the first four to six months of life and satisfying by itself the nutritional requirements of this category of person. The term "follow-on formula" means a foodstuff intended for use by infants aged over four months and constituting the principal liquid element in the progressively diversified diet of this category of person.

Requirements for infant formulas are well known to the skilled person. For example, recommendations and requirements are provided by The European Society for Pediatric Gastroenterology, Hepatology and Nutrition (ESPGHAN) e.g. Koletzko, B., et al., 2005. "Global standard for the composition of infant formula: recommendations of an ESPGHAN coordinated international expert group" Journal of pediatric gastroenterology and nutrition, 41(5), pp. 584-

599. Typically, an infant formula in a ready-to-consume liquid form (for example reconstituted from a powder) provides 60-70 kcal/100 ml. Infant formula typically comprises, per 100 kcal: about 1.8-4.5 g protein; about 3.3-6.0 g fat (lipids); about 300-1200 mg linoleic acid; about 9-14 g carbohydrates selected from the group consisting of lactose, sucrose, glucose, glucose syrup, starch, maltodextrins and maltose, and combinations thereof; and essential vitamins and minerals.

In some embodiments, the ingestible infant composition further comprises one or more carriers. As used herein the term "carrier" is any substance useful as an excipient, filler, bulking agent, diluent, colouring agent, stabiliser, thickener, binder, flavouring agent and the like. Preferably, the one or more carriers comprise skimmed milk powder and/or lactose. Most preferably, the carrier is skimmed milk powder and/or lactose.

The ingestible infant composition may be in a powdered form, wherein the powdered form can be reconstituted into a liquid format prior to ingestion. In preferred embodiments, the ingestible infant composition is reconstituted with water prior to ingestion. Preferably, the composition is reconstituted with water to provide one serving.

In other preferred embodiments, the composition is in a ready to drink form. The ready to drink composition may be provided in a bottle.

First and Second Medical Uses

First Medical Use

In an embodiment, the invention provides a composition for use in therapy.

Second Medical Use Against Infection

In another aspect, the invention provides a composition for use in preventing and/or reducing a non-viral infection, wherein the composition is obtained or obtainable using the method of the invention.

In some embodiments, the non-viral infection is a bacterial infection, a parasite infection or a fungal infection.

The non-viral infection may be a bacterial infection selected from an *Escherichia coli* infection, a *Vibrio cholerae* infection, a *salmonella* infection, a clostridia infection, a *shigella* infection, a parasite infection, including *Giardia lamblia, Entamoeba histolytica* and *Cryptosporidium* spp or mixtures thereof.

Typical bacterial infectious diseases that can be treated or prevented by the invention include *salmonellosis*, shigellosis, typhoid fever, bacterial meningitis, anthrax, botulism, brucellosis, campylobacteriosis, cat scratch disease, cholera, diphtheria, epidemic typhus, gonorrhea, impetigo, legionellosis, leprosy (Hansen's Disease), leptospirosis, listeriosis, lyme disease, melioidosis, rheumatic fever, MRSA infection, nocardiosis, pertussis (whooping cough), plague, pneumococcal pneumonia, psittacosis, Q fever, Rocky Mountain Spotted Fever (RMSF), scarlet fever, syphilis, tetanus, trachoma, tuberculosis, tularaemia, typhus and/or urinary tract infections.

Typical parasitic infectious diseases that can be treated or prevented by the invention include African trypanosomiasis, amebiasis, ascariasis, babesiosis, Chagas disease, clonorchiasis, cryptosporidiosis, cysticercosis, diphyllobothriasis, dracunculiasis, echinococcosis, enterobiasis, fascioliasis, fasciolopsiasis, filariasis, free-living amebic infection, giardiasis, gnathostomiasis, hymenolepiasis, isosporiasis, kala-azar, leishmaniasis, malaria, metagonimiasis, myiasis, onchocerciasis, pediculosis, pinworm infection, scabies, schistosomiasis, taeniasis, toxocariasis, toxoplasmosis, trichinellosis, trichinosis, trichuriasis, trichomoniasis and/or trypanosomiasis.

Typical fungal infectious diseases that can be treated or prevented by the invention include aspergillosis, blastomycosis, candidiasis, coccidioidomycosis, cryptococcosis, histoplasmosis and/or tinea pedis.

In another aspect, the invention provides the infant formula of the invention for use in reducing or preventing a non-viral infection.

In another aspect, the invention provides a method of treating or preventing a non-viral infection comprising the step of administering the composition or infant formula of the invention to a subject in need thereof.

Second Medical Use Against Inflammation

In another aspect, the invention provides a composition for use in preventing and/or reducing inflammation, wherein the composition is obtainable or obtained using the method of the invention.

Typical inflammatory conditions that may be treated or prevented by the use of the invention include, but are not limited to, acute inflammations such as sepsis, infections, burns and chronic inflammations such as inflammatory bowel disease, Crohn's disease, ulcerative colitis, necrotising enterocolitis, skin inflammation, such as UV or chemical-induced skin inflammation, eczema, reactive skin, psoriasis, vitiligo, acne, liver inflammation, alcoholic cirrhosis, allergy, atopy, bone inflammation, rheumatoid arthritis, systemic lupus, Gougerot-Sjögren's syndrome, Reiter's syndrome, poliomyelitis, dermato-myositis, thyroIditis, Basedow, Hashimoto, type I diabetes, Addison's disease, auto-immunes hepatitis, celiac disease, Biermer's disease, multiple sclerosis, myasthenia, encephalomyelitis, eye inflammation, obesity-associated inflammation, age-related low-grade inflammation, Blau's syndrome, Alzheimer's disease, cardiovascular diseases, atherosclerosis, metabolic syndrome, gingivitis, paronditis and combinations thereof.

The composition of the invention is particularly effective in preventing and/or treating inflammatory conditions selected from chronic inflammatory conditions such as inflammatory bowel disease, Crohn's disease, ulcerative colitis, necrotizing enterocolitis, eczema, allergy, and atopy The composition of the invention may also be used to control and/or alleviate an inflammatory reaction of the body.

The composition of the invention can further be used to generate, improve or reinforce homeostasis and oral tolerance.

In another aspect, the invention provides the infant formula of the invention for use in reducing or preventing inflammation.

In another aspect, the invention provides a method of reducing or preventing inflammation comprising the step of administering the composition or infant formula of the invention to a subject in need thereof.

Other Medical Uses

In some embodiments, the composition generates, improves or reinforces homeostasis and oral tolerance.

In some embodiments, the composition controls and/or alleviates an inflammatory reaction.

In some embodiments, the composition increases the immune function of a subject.

In another aspect, the invention provides a composition for use in increasing immune function of a subject, wherein the composition is obtainable using the method of the invention.

In another aspect, the invention provides the infant formula of the invention for use in increasing immune function of a subject.

In another aspect, the invention provides a method of increasing immune function of a subject comprising the step of administering the composition or infant formula of the invention to a subject in need thereof.

Method of Treatment

It is to be appreciated that all references herein to treatment include curative, palliative and prophylactic treatment. The treatment of mammals, particularly humans, is preferred. Both human and veterinary treatments are within the scope of the invention.

As used herein, the term "prevent" includes prevention and reducing the risk of a condition.

Subject

A "subject" refers to either a human or non-human animal.

The composition may be administered to humans or non-human animals, in particular companion animals or livestock animals. The composition has beneficial effects for any age group. Preferably, the composition is intended for infants, juveniles, adults or elderly. It may however also be administered to mothers during pregnancy and lactation to treat the infant.

Examples of non-human animals include vertebrates, for example mammals, such as non-human primates (particularly higher primates), dogs, rodents (e.g. mice, rats or guinea pigs), pigs and cats.

A "companion animal" is any domesticated animal, and includes, without limitation, cats, dogs, rabbits, guinea pigs, ferrets, hamsters, mice, gerbils, horses, cows, goats, sheep, donkeys, pigs and the like.

Preferably, the subject is a human.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

All publications mentioned in the above specification are herein incorporated by reference. Various modifications and variations of the disclosed methods, compositions and uses of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

EXAMPLES

Introductory Part: Description of SIgA
Quantitations by ELISA (Presence of SIgA) or by
TSLP Excretion Bioassays (Bioactivity of SIgA)

Presence and quantitation of SIgA molecules (or at least of parts of SIgA molecules) were measured by ELISA using a commercial kit for bovine IgA (Bovine IgA ELISA Quantitation Set, Bethyl Laboratories Inc., cat no E10-131). Kit protocol was followed with the adaptation that the kit IgA standard was replaced by native bovine SIgA (purified by classical size exclusion chromatography under native conditions, as described in Favre et al., 2003, J. Chromatogr. B Analyt. Technol. Biomed. Life. Sci., March 25; 786(1-2): 143-51) to allow correct quantitation of SIgA (and not only IgA). SIgA standard curve was set to typically cover SIgA range from 1000 to 10 ng/ml. Kit validation checks demonstrated that milk matrix was not interfering with quantitation at the dilutions used for the samples (typically between 1:1'000 and 1:20'000).

Noteworthy, detection of SIgA molecules by ELISA is not at all predictive of integrity of the SIgA molecules, hence of their bioactivity. For example, a degraded SIgA molecule would be detected as long as it would still be recognized by the polyclonal detection antibodies used for the ELISA kit. Furthermore, degraded or even cleaved SIgA molecules may expose epitopes normally not accessible to the detection antibodies when SIgA molecules are in native format. All this could lead to artificially increased SIgA quantitation (as illustrated in Example 3 and FIG. 5 below).

To circumvent this issue and aligned with the original concept of the increased efficacy of probiotics by association with native bioactive SIgA molecules, a bioassay was developed to assess bioactivity of SIgA molecules (see details of the experimental procedure in Mathias et al, 2010, JBC, vol. 285, no. 44, pp. 33906-33913). Briefly, Human colonic adenocarcinoma epithelial Caco-2 cells (HTB 37, American Type Tissue Collection) were grown at 37° C. in complete DMEM (C-DMEM) medium consisting of DMEM-Glutamax medium (Sigma) supplemented with 10% fetal bovine serum (FBS, Sigma), 1% non essential amino acids (Sigma), 10 mM HEPES (pH 7.0, Sigma), 0.1% transferrin (Invitrogen AG, Basel, Switzerland) and 1% streptomycin/penicillin (Sigma), and used between passages 23 and 37. Cells cultivated to 80% confluency were seeded on Transwell filters (diameter, 12 mm; pore size, 0.4 µm; Corning Costar, Cambridge, Mass.) at a density of 0.8E5 cells/cm$^2$. The culture medium was changed every 2 days. The formation of a polarized Caco-2 cell monolayer at week 3 was established by morphology and monitoring of the transepithelial electrical resistance (TER; ohms×cm$^2$) using a Millicell-ERS apparatus (Millipore, Bedford, Mass.). TER values of well-differentiated monolayers were in the range of 380-450 ohms×cm$^2$. Of note, this process leads to the creation of an in vitro tight epithelium with separated apical and basolateral culture compartments, reflecting gut luminal and mucosal compartments respectively. Prior to exposition to probiotics or probiotics-SIgA complexes, the apical compartment of Caco-2 cell monolayers was washed twice with phosphate buffer saline (PBS; 116.3 mM NaCl, 10.4 mM Na$_2$HPO$_4$, 3.2 mM KH$_2$PO$_4$, pH 7.4), and C-DMEM was replaced with typically 500 µl of the same medium lacking FBS and antibiotics (DMEM-A$^-$).

Addition of probiotics to the apical compartment of the culture system (see detailed protocol below) leads to secretion of several immune factors in the basolateral compartment, including Thymic Stromal LymphoPoietin (TSLP), known to play an important role in maintaining an intestinal non-inflammatory environment while favouring maturation of dendritic cells, the key conductor of any immune response. Hence, after overnight incubation with the probiotics, TSLP release is dosed by ELISA using commercial kit for human proteins.

Preparation of fresh probiotic biomass was typically obtained by over-night culture of the bacterial strain *Bifidobacterium lactis* CNCM I-3446, thereafter called BL818, in Mann-Rogosa-Sharpe broth medium (Difco Laboratories, Detroit, Mich.) complemented with 0.05% L-cysteine, at 37° C. and without agitation. Assessment of colony forming units (CFU) per milliliter resulting from such culture conditions was carried out by correlation of the measurement of the optical density at 600 nm with plating of successive dilutions of the overnight incubations.

To assess SIgA bioactivity, probiotics (typically 2E7 CFU of fresh biomass or 2E8 CFU of spray-dried bacteria) and SIgA were mixed in a final volume of 100-500 µl of PBS, in a 1.5 ml low protein-binding test tube and incubated for 30 minutes at 37° C., if not specified differently. Alternatively, probiotics alone (reference) or already pre-formed probiotics-SIgA complexes were simply diluted in PBS to get the desired probiotics counts in the 100-500 µl final volume. Probiotics-SIgA complexes formed during this incubation step, or already pre-existing, were then pelleted by centrifugation (typically 6000 g for 5 minutes) and supernatant containing unbound SIgA was discarded. Probiotics-SIgA complexes were re-suspended in 500 µl of DMEM-A$^-$ culture medium before addition to the apical compartment of the Caco-2 culture for overnight incubation (typically 16 hours) at 37° C. in a cell-culture incubator.

After overnight incubation, culture medium from basolateral compartment of the polarized Caco-2 cells was collected and stimulated TSLP production (concentration expressed as pico-grams per ml of culture medium) was then measured by ELISA using commercial kits for human TSLP (Biolegend, San Diego, Calif.).

Figure 2:
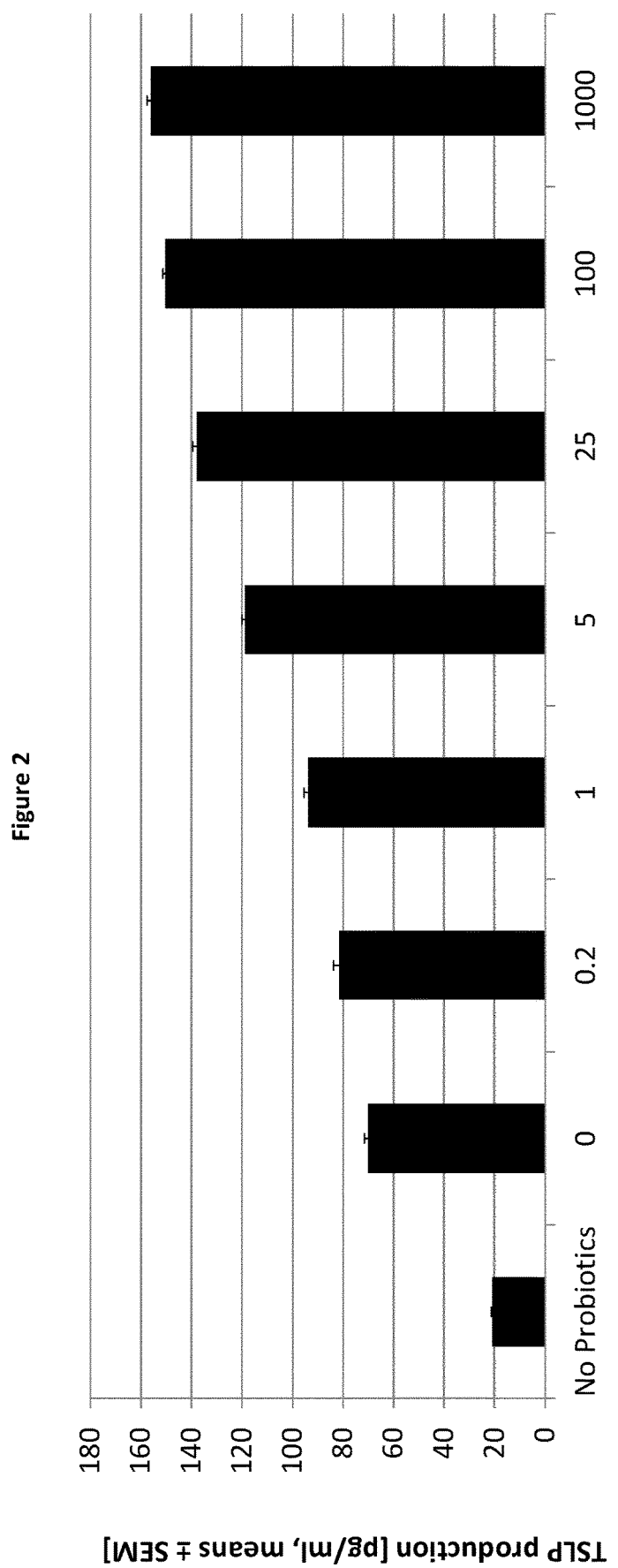

Pre-association of SIgA with probiotics increase TSLP production by Caco-2 cells in a dose-dependent manner in comparison to probiotics alone. Consequently, a standard curve made with fixed quantity of probiotics associated with growing quantities of native bovine SIgA (same as used for the ELISA quantitation) was used as reference to dose the quantity of bioactive SIgA present in a test sample based on the TSLP production induced (FIG. 2). Alternatively, the bioassay was also run without standard curve, then only allowing a semi-quantitative comparison of SIgA bioactivity between different test samples. Bioassay tests were performed at least in technical duplicate, preferentially in triplicate.

Example 1: Process According to the Present Invention

Raw milk was received from a Swiss farm and centrifuged at 15° C. to obtain raw skim milk. The raw skim milk was concentrated to 24% dry matter at 15° C. using a Reverse Osmosis (RO) concentration plant (Tetra Alcross RO with spiral membrane Alfa Laval RO98pHt-3838/30—TetraPak, Lund, Sweden). The 24% RO skim milk was preheated in a plate heat exchanger to 55° C. and heated to 83° C. with Direct Steam Injection. After passing a holdtube providing an average residence time of 6 s, the RO skim milk was instantaneously cooled to 55° C. by using a flash vessel, as common in the dairy industry. The RO skim milk was further cooled to 5° C. in a plate heat exchanger before spray-drying it under gentle conditions, without prewarming, on an open-top spray-dryer such as described in U.S. Pat. No. 2,353,495 to yield RO skim milk powder. Egron exhaust air temperature and relative humidity were 12% and 65° C. The RO skim milk powder contained 139 µg SIgA/g powder as determined by ELISA and 25 µg bioactive SIgA/g powder as determined by bioassay analysis.

In parallel, BL818 probiotics were produced by fermentation, centrifuged to concentrate the bacteria to provide liquid fresh biomass at 5° C. with 1.4E11 CFU/g of BL818, as measured by flow cytometry and confirmed later with plate count analysis.

The RO skim milk powder was dissolved in warm water, and liquid BL818 suspension was added to it such as to yield a 34% dry matter suspension containing 5E8 CFU/g BL818 and 340 ng bioactive SIgA per 2E7 CFU BL818. The suspension was kept at 37° C. during 30 minutes and cooled to 5° C. in a plate heat exchanger before spray-drying it in a spray-dryer under gentle conditions as described above. This yielded a powder containing probiotics with higher bioactivity than spray-dried probiotics alone, as tested in the bioassay (136.7±1.8 vs. 77.7±4.8 pg/ml TSLP production respectively).

Example 2: Effect of Microfiltration of Skimmed Milk on SIgA Content

Raw skimmed milk (8.0-8.7% total solids) and Reverse Osmosis (RO) skim milk (about 24% total solids) were used for these experiments. The milks were subjected to microfiltration (MF) using different membranes at temperatures between 52 and 55° C. The SIgA content in the milk before filtration and after filtration in the different phases were measured by ELISA, as described above. The percentage of the SIgA in the permeate after microfiltration (SIgA yield [%]) was calculated versus the amount of SIgA in the milk before filtration. The microbial contamination of the milk was also assessed and the log reduction of the bacterial content was calculated (total plate count reduction [log]). The results are provided in Table 2 below and in FIG. 3.

The trial with the membrane providing the best results was repeated at a temperature of 14° C., to assess the impact of the temperature on conservation of SIgA and on reduction of the microbial contamination.

The milk types were warmed to process temperature on a plate heat exchanger and microfiltered on a microfiltration rig using different membranes.

Details of the membranes used and key processing parameters are shown in Table 1 below.

TABLE 1

Membrane supplier and type, and processing parameters of the microfiltration trial

| | Membrane | | | | Processing | | |
|---|---|---|---|---|---|---|---|
| Supplier | Type | Material | Surface m² | Pore size nm | Temp. °C. | TMP bar | Circulation L/h |
| Tami 0.14 micron | Tami spiral module Ø 25 mm, 8 channels, 19 modules, 1178 mm length | Ceramic | 2 × 3.8 | 140 | 55 | 1.5 | 2000-6000 |
| Alfa-Laval | MFP05-3838 (fluoropolymer) | Polymer | 2 × 4.7 | 500 | 52 | 0.9 | 12000 |
| Microdyn - Nadir | MV020 - 3838 (PVDF) | Polymer | 2 × 5.7 | 200 | 52 | 0.9 | 12000 |
| Tami 1.4 micron | Tami spiral module Ø 25 mm, 23 channels, 1178 mm length | Ceramic | 19 × 0.35 | 1400 | 55 | 0.14 | 2000-6000 |

The device was sanitised prior to use in order to make an assessment of the process effect on retentate and permeate bacterial load. To do so, the device was circulated with 1% P3-Oxonia solution (Ecolab, Saint Paul, MN, USA) overnight.

The results of the microfiltration experiments are provided in Table below.

TABLE 2

Summary of process conditions and results of the microfiltration experiments

| Membrane | Milk dry matter [%] | Microfiltration temperature [° C.] | SIgA in milk (before) [µg/mL] | SIgA in permeate (after) [µg/mL] | SIgA yield [%] | Plate count reduction [log] |
|---|---|---|---|---|---|---|
| Tami 0.14 micron | 8.3 | 55 | 254 | 142 | 55.9 | 3.3 |
| MFP05 | 8.4 | 52 | 294 | 133 | 45.2 | 4.2 |
| MV020 | 8.7 | 52 | 375 | 124 | 33.1 | 4.7 |
| MMS/Tami 1.4 micron | 23.9 | 55 | 1537 | 1058 | 68.8 | 1.8 |
| MMS/Tami 1.4 micron | 24 | 14 | 1441 | 1010 | 70.1 | 2.0 |

The results show that small pore sizes provide the highest reduction of microbial contamination, but lead to the largest loss of SIgA during the microfiltration process. Larger pores are less efficient in reducing the microbial contamination, but allow retention of larger amounts of SIgA (higher SIgA yield) in the milk after microfiltration. In particular, microfiltration using a membrane with a pore size of 500 nm or smaller leads to such low yields of SIgA in the milk after the microfiltration, that milk becomes an uneconomical source of SIgA to use in a process according to the invention. In contrast, the ceramic membrane with pore sizes of 1400 nm (MMS) did not affect SIgA contents as much, with a SIgA yield in the milk after microfiltration of 69%. The reduction of microbial load, even though smaller than with the other tested membranes, was close to 2 log. Such microbial reduction is sufficient for the obtained milk to be used in the process of the present invention. In particular, after being subsequently subjected to a heat treatment step, such as described in the present application and in particular in Example 3 below, the milk obtained by microfiltration with the MMS membrane is suitable for use in sensitive products such as infant formula. The reduction of the microbial load of 2 log achieved with the MMS membrane is sufficient to make it possible to use mild conditions for the heat treatment step such as to keep bioactive SIgA while still obtaining an infant formula-grade composition starting from any milk of standard microbiological quality. Thus, the membrane with pore size of 1400 nm provided the best balance between reduction of microbial load and avoidance of SIgA loss.

Example 3: Comparison of Different Conditions for Heat Treatment of Reverse Osmosis (RO) Skimmed Milk Raw milk was centrifuged at 15° C. to obtain raw skim milk. The raw skim milk was concentrated from 9% dry matter to 22.9% dry matter at 15° C. using a Reverse Osmosis (RO) concentration plant (see example 1). The RO skim milk was subjected to four different heat treatments using direct steam injection and flash cooling:

Sample 1: 74° C./103 s
Sample 2: 83° C./6 s
Sample 3: 87° C./2 s
Sample 4: 90° C./0.96 s The liquid, pasteurized RO skim milk was cooled to 5° C. and the cold concentrate was spray-dried.

Figure 4:
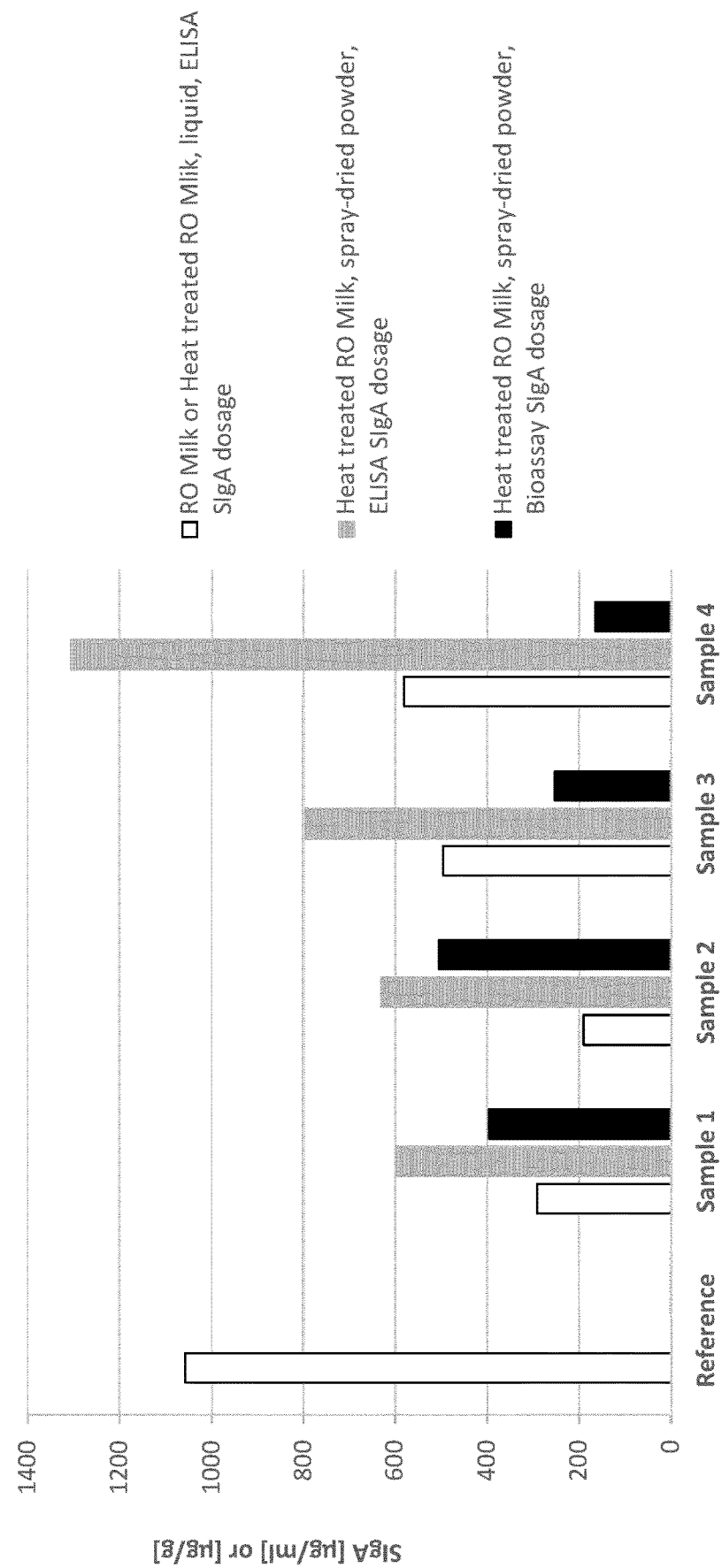

Presence of SIgA molecules in the original RO skimmed milk (Reference), in the heat treated RO skimmed milk (Samples 1 to 4) and in the final powders obtained from Samples 1 to 4 were assessed by ELISA. Quantitation of SIgA bioactivity in the heat treated RO skimmed milk and in the final powders was assessed through the TSLP excretion bioassay as described above. The associated ELISA and TSLP excretion results are shown in FIG. 4.

The results of the quantitation of SIgA by ELISA show that a heat treatment at 90° C. for 0.96 s (Sample 4) led to the highest amounts of SIgA both in the heat treated milk and in the powder. Surprisingly, SIgA bioactivity assessment (TSLP excretion bioassay) revealed that intermediate conditions are more favourable to preserve maximum bioactive SIgA, with a heat treatment of 83° C. for 6 s (Sample 2) regarded as preferred choice. This shows that a portion of the SIgA detected by ELISA in the samples submitted to high temperatures is in fact inactive and that the TSLP excretion bioassay used herein appears as a more reliable method to define the amount of really effective SIgA in the composition. Such data demonstrates that ELISA SIgA quantitation is not correlating with SIgA molecules integrity and thus bioactivity.

In terms of microbiology, all heat treatments described above induced a total plate count (TPC) reduction of 2.0-2.1 log, while providing a reduction of the pathogens, which are more sensitive to heat than other microbes, of at least 7 log. The spray-dried powders were demonstrated to be free of Enterobacteriaceae, *Enterobacter sakazakii* and *Salmonella*.

Example 4: Influence of Temperature and Time on Formation and Bioactivity of SIgA-BL818 Complexes Association of SIgA and BL818 in RO skimmed milk was tested at the ratio of 34 ng of SIgA per 2E7 CFU of BL818, under various time and temperature conditions (37° C., 20° C. and 12° C., for 60, 30 and 15 minutes at each temperature). Of note, neither temperatures above 37° C. were tested in this experiment, as such temperatures would be deleterious to the probiotic, nor temperatures below 12° C., as pretests done at 4° C. did not show any association to take place (data not shown).

The experiment was performed based on three identical samples of RO skimmed milk admixed with BL818 liquid biomass. For each sample, 41.9 g of a skim milk powder heat-treated according to the preferred conditions identified in Examples 3 (Sample 2) containing 285 μg of bioactive SIgA per gr of powder (as determined by the TSLP excretion bioassay) was dissolved in 65 ml of distilled water. A volume of 23.3 ml of a BL818 probiotic biomass (thawed frozen stock) containing 3E11 CFU/ml was then added to achieve the desired SIgA to BL818 ratio. Right after addition of the BL818 biomass, the three mixes were incubated at 37° C., 20° C. or 12° C., respectively, under light agitation. After 15, 30 or 60 minutes of incubation, during which Probiotics-SIgA association could take place, two samples (duplicated) were collected from each mix, and centrifuged at 6000 g for 5 minutes at 4° C. to pellet the already formed probiotics-SIgA complexes and to stop the association process. After discarding the supernatant containing the unbound SIgA, the pellet was resuspended in bioassay cell culture medium and equivalent of 2E7 CFU from each sample were tested in the bioassay as described above.

The bioactivity of SIgA complexes, as assessed by the TSLP excretion bioassay after the association step for each sample, provided an indirect evaluation of the level of association of SIgA with BL818 in the form of complexes.

Figure 5:
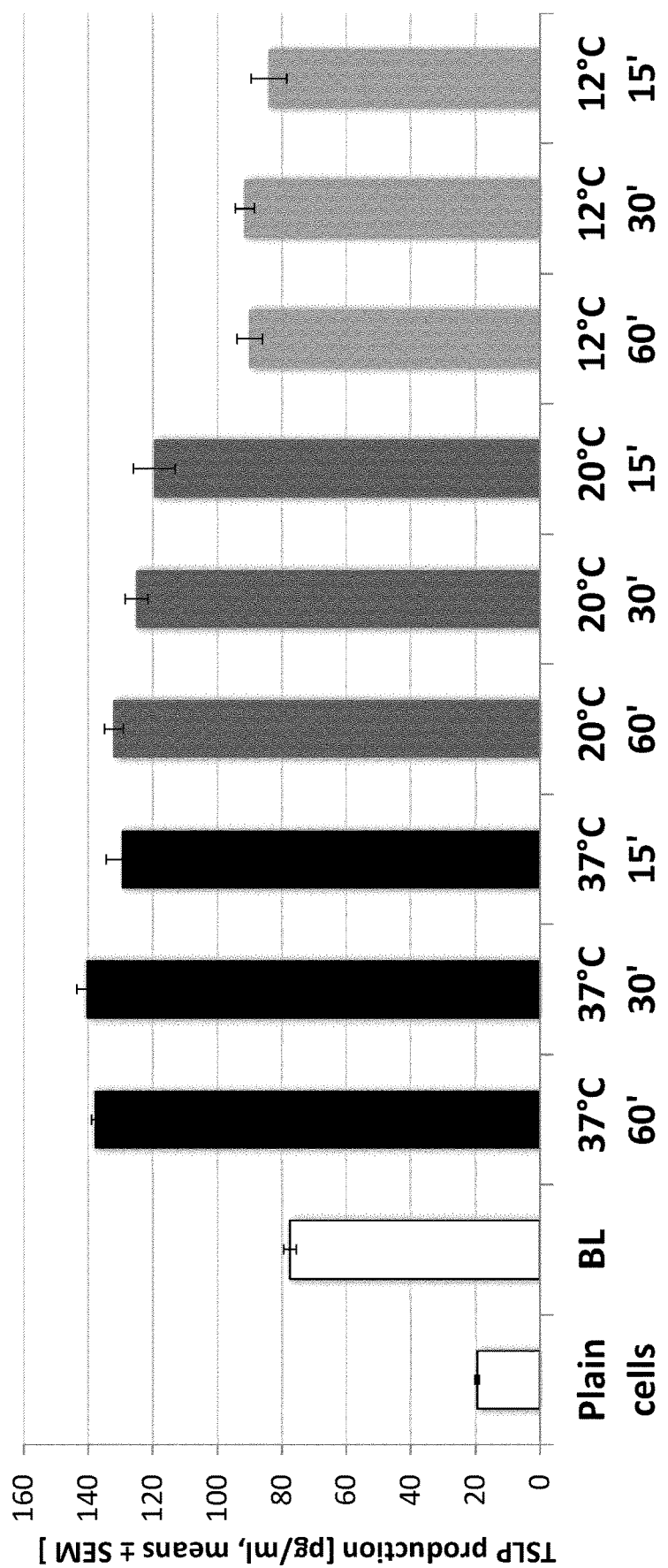

Results presented in FIG. 5 show that probiotics-SIgA complexes formation increased with the augmentation of the temperature during the association step. The best temperature for the association step was found to be 37° C. Complex formation was less efficient when decreasing the temperature to 20° C. and further to 12° C. However, complexation at 12° C. was still sufficient to achieve a bioactivity superior to that of BL818 alone, which is indicated by the horizontal grey line in FIG. 5.

The trial also revealed that durations of the association step, ranging from 15 to 60 minutes, led to successful complex formation, even though complexation tended to be slightly reduced in trials where the duration was set to 15 minutes.

All taken together, the optimum conditions for the probiotics-SIgA association step were found to be 30 minutes at 37° C.

Example 5: Influence of the BL818 Concentration (in CFU/mL) on Formation and Bioactivity of SIgA-BL818 Complexes We sought to study the influence of the concentration of BL818 on efficiency of probiotics-SIgA complex formation. Lab association trials were thus run with constant ratio of SIgA to BL818 (34 ng SIgA/2E7 CFU BL818), constant total solids content and constant association conditions as identified as being the best in example 4 (30 minutes at 37° C.), but with BL818 concentrations of 5.4E10, 5.4E9 and 5.4E8 CFU/ml, respectively. Test samples were prepared as described in Table 3.

TABLE 3

Composition of samples used to test influence of BL818 concentration on formation and bioactivity of SIgA-BL818 complexes

| | Distilled water [ml] | RO Skim milk powder with 285 μg bioactive SIgA/g [g] | RO Skim milk without bioactive SIgA [g]* | BL818 biomass with 3.05E11 CFU/g [g] |
|---|---|---|---|---|
| Control 1 (5.4E10 CFU/ml BL818 without SIgA) | 65.2 | 0.0 | 41.9 | 22.9 |
| Control 2 (5.4E8 CFU/ml BL818 without SIgA) | 87.9 | 0.0 | 41.9 | 0.229 |
| Test 1 (5.4E10 CFU/ml with SIgA) | 65.2 | 41.9 | 0.0 | 22.9 |

TABLE 3-continued

Composition of samples used to test influence of BL818 concentration on formation and bioactivity of SIgA-BL818 complexes

| | Distilled water [ml] | RO Skim milk powder with 285 μg bioactive SIgA/g [g] | RO Skim milk without bioactive SIgA [g]* | BL818 biomass with 3.05E11 CFU/g [g] |
|---|---|---|---|---|
| Test 2 (5.4E09 CFU/ml with SIgA) | 86.0 | 4.169 | 37.53 | 2.29 |
| Test 3 (5.4E08 CFU/ml with SIgA) | 87.6 | 0.417 | 41.75 | 0.229 |

*RO Skim milk heat-treated at 145° during 6 seconds, leading to undetectable SIgA signals both at ELISA and Bioassay levels.

After incubation, samples were centrifuged to stop the association process as described in example 4 and subjected to the TSLP excretion bioassay (samples normalized to get 2E07 CFU tested on bioassay). Bioactivity of the obtained complexes was thus indicative of the efficiency of complex formation.

Figure 6:
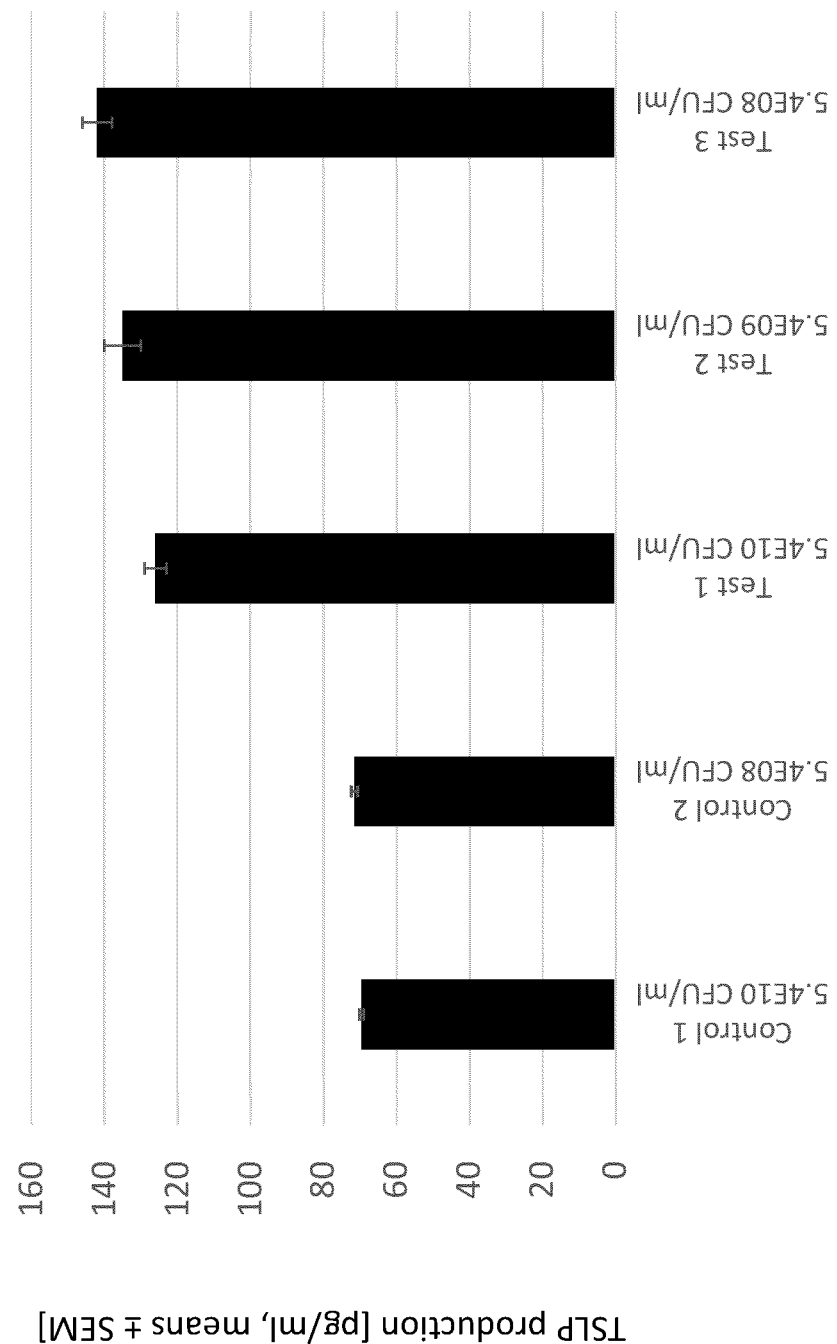

Results of FIG. 6 show that concentration of BL818 during the association step affected complex formation efficiency, with a tendency to improve it with the reduction of the BL818 concentration. Indeed, the best bioactivity was observed at a BL818 concentration of 5.4E8 CFU/mL ($142\pm4$ pg/ml TSLP), followed by the concentration of 5.4E9 ($135\pm5$ pg/ml TSLP) and then that of 5.4E10 CFU/mL ($126\pm3$ pg/ml TSLP). However, it remains that all BL818 concentrations allowed substantial increased bioactivity of BL818-SIgA complexes in comparison to the BL818 alone controls.

Example 6: Influence of the BL818 Format (Liquid Biomass or Spray-Dried) on Formation and Bioactivity of SIgA-BL818 Complexes In order to compare the influence of the probiotic format on efficiency of probiotics-SIgA complex formation, lab association trials were run with constant ratio of SIgA to BL818 (34 ng SIgA/2E7 CFU BL818), constant total solids content and constant association conditions as identified in examples 4 and 5 (30 minutes at 37° C., 5.4E08 CFU BL818/ml), but with BL818 from either liquid biomass in powder form (spray-dried on Mini spray-drier B-290, Büchi, CH-Flawil). Samples were prepared as described in Table 4.

TABLE 4

Composition of samples used to test influence of BL818 format (biomass or spray-dried) on formation and bioactivity of SIgA-BL818 complexes.

| | Distilled water [ml] | RO Skim milk powder with 285 μg bioactive SIgA/g [g] | RO Skim milk without bioactive SIgA [g]* | BL818 biomass with 3.05E11 CFU/g [g] | BL818 spray-dred powder with 9.45E+11 CFU/g [g] |
|---|---|---|---|---|---|
| Control (5.4E08 CFU/ml BL818 without SIgA) | 87.9 | 0.0 | 41.9 | 0.229 | 0.0 |
| Test Biomass (5.4E08 CFU/ml with SIgA) | 87.6 | 0.417 | 41.75 | 0.229 | 0.0 |
| Test Powder (5.4E08 CFU/ml with SIgA) | 87.1 | 0.417 | 41.75 | 0.0 | 0.740 |

After incubation, samples were centrifuged to stop the association process as previously described in Example 4 and subjected to the TSLP excretion bioassay (samples normalized to get 2E07 CFU tested on bioassay). Bioactivity of the obtained complexes was thus indicative of the efficiency of complex formation.

Figure 7:

Results provided in FIG. 7 show that the format of BL818 used for the association step affected complex formation efficiency, with a tendency to decrease when BL818 is in a spray-dried powder format. However, it remains that both BL818 formats resulted in substantially increased bioactivity of BL818-SIgA complexes in comparison to the BL818 alone control.

Example 7: In Vivo Effect of Compositions of the Present Invention for the Prevention and Treatment of Infection and Inflammation The physiological effect of a starter infant formula comprising BL818-SIgA complexes obtained by the process of the present invention as compared to a starter infant formula with probiotics alone was tested in vivo in a mouse model for neonatal immune maturation.

In this model, mouse pups born in a 3 days time window from synchronized germ-free C3H-HEN dams were considered for the study. At day 5 of age, litters were equilibrated in terms of size as well as of gender and pup birth date. Pups were kept in germ-free conditions with their dams until one week of age. Then, the full litters were transferred into specific pathogen-free housing conditions and exposed to mouse fecal material containing intestinal bacteria to permit natural microbial colonization. At the same time, pups started to be supplemented daily with mouth instillation of 20 μl of one of the test infant formula preparations (see details and table 5 below) for 14 days, until weaning at day 21 of age. Of note, keeping the litters in germ-free conditions until day 7 before starting microbial colonization and supplementation had two objectives. First, this was to mimic human immune status at birth as closely as possible. Indeed, human infants are born with an immune system a bit more mature than mouse pups, but studies have shown that this gap was minimized after one week of age of mouse pups. Second, germ-free animals have an underdeveloped immune system, in part characterized by an absence of mucosal IgA production, as such IgA are comprised in the dam's milk secretion. Hence, keeping mouse dams in germ-free condition as long as possible allowed ensuring limited interference from milk endogenous SIgA over the SIgA present in the probiotics-SIgA complexes, allowing unbiased comparison between probiotics given alone or pre-associated with SIgA.

TABLE 5 testing groups of the in-vivo experiments.

| Group | | Group details | Reason to be |
|---|---|---|---|
| 1) Infant formula (IF) prototype alone | Comparative | Negative control for IF matrix | Validates that IF matrix does not interfere with the planned readouts |
| 2) IF prototype with BL alone (1E4 CFU/day) | Comparative | BL reference in IF matrix | Reference for effect of BL + SIgA prototypes |
| 3) IF prototype with SIgA[1] alone (500 pg/day) | Comparative | SIgA reference in IF matrix | Reference for effect of BL + SIgA prototypes |
| 4) IF prototype with BL (1E4 CFU/day) and SIgA (500 pg/day) dry-mixed | Comparative | IF prototype with BL and SIgA without association prior to administration | Test of efficacy of SIgA + BL administered un-associated over BL alone |
| 5) IF prototype with BL (1E4 CFU/day) and SIgA (500 pg/day) complexed using optimized process of Example 1 | Invention | IF prototype with BL and SIgA associated prior to administration | Test of efficacy of SIgA + BL optimized complexation process according to the invention. |

[1]SIgA dosages refer to bioactive SIgA; SIgA are quantified using the TSLP bioassay in bovine milk subjected to a heat treatment at 83° C. for 6 s and the desired bioactive SIgA dose is obtained by using an adequate amount of such milk in the infant formula prototype (see Table 6 below).

To obtain the IF prototypes, compositions as described in Table 6 below were dry-mixed in the laboratory. IF prototypes containing BL818 alone or in conjunction with bioactive SIgA [groups 5), 6) and 7)] targeted a BL818 content of 2E7 CFU BL818/g formula, which is a standard probiotic concentration target for infant formula containing BL818 probiotics.

TABLE 6

Composition of IF prototypes 4) to 8)

| Ingredients for dry-mixing | Amount in Group 1 [g] | Amount in Group 2 [g] | Amount in Group 3 [g] | Amount in Group 4 [g] | Amount in Group 5 [g] |
|---|---|---|---|---|---|
| Infant formula base matrix (whey predominant, non-hydrolysed) | 300.00 | 299.72 | 295.89 | 295.61 | 295.62 |
| Probiotic preblend (spray-dried BL818 in maltodextrin; 2.11E10 CFU BL818/g) | — | 0.2844 | — | 0.2844 | — |
| Processed bovine milk (24.84 µµg bioactive SIgA per g of milk) | — | — | 4.106 | 4.106 | — |
| BL818-SIgA powder produced in Example 1 (340 ng bioactive SIgA, 2E7 CFU BL818, 1.4E9 CFU BL818 per gram of powsder) | — | — | — | — | 4.380 |
| Total | 300 | 300 | 300 | 300 | 300 |

The infant starter formula powder itself was formulated as follows. All ingredients are typical ingredients used in whey-predominant, non-hydrolysed, probiotic-free infant starter formula.

TABLE 7

Infant starter formula base for in-vivo experiments

| Ingredient | Solids [%] |
|---|---|
| Milk Skimmed Liquid 18% Solids Non Fat | 10.807 |
| Lactose Powder | 36.986 |
| Cream Liquid 36% Fat | 8.996 |
| Whey Powder Demineralized | 20.641 |
| Vegetable Oil Mix | 16.759 |
| Lecithin Soy Liquid | 0.705 |
| Oil Mix LC-PUFA | 0.686 |
| Tricalcium Citrate Dry | 0.585 |
| Choline Bitartrate | 0.395 |
| Potassium Chloride | 0.277 |
| Vitamin Mineral Premix | 0.235 |
| Tripotassium Citrate | 0.149 |
| Trisodium Citrate | 0.121 |
| Disodium Phosphate 2 Hydrate | 0.101 |
| Magnesium Chloride | 0.056 |
| Moisture | 2.5 |
| Total input ingredients (solids) | 97.5 |

Test infant formula preparations were all reconstituted by thorough mixing to allow total dissolution of the powder. They were diluted 40 times in 37° C. pre-heated water in order to get the equivalent of 1E4 CFU of probiotics in the 20 µl daily supplementation (probiotic dose adapted to mouse newborns). Test infant formula was given to the mouse pups within maximum 5 minutes after reconstitution to first mimic real-life bottle feeding practices and second, to prevent probiotics and SIgA to associate prior to administration in test Infant Formula 4.

At day 21 of age, supplementation was stopped and pups were weaned, with males and females housed in separate cages. Pups were then kept under normal housing conditions and sacrificed at 54 days of age. In order to assess the differential impacts of pre-weaning infant formula supplement on mucosal and systemic immune maturation, Peyer's patches (PPs, intestinal immune inductive sites) and blood were collected in ice-cold DMEM medium (PAA Laboratory, cat. no. E15-883) containing 10% of inactivated fetal calf serum (FCS, Amimed 2-01F10-1) and in heparinized tubes (Milian, cat no. HEP-75PP), respectively and kept at 4° C. until further use.

In order to isolate immune cells from collected PPs, the latter were first incubated for 1 h 30 at 37° C. in 1 ml of DMEM medium containing 5 mM $CaCl_2$) (Merck, cat. no. 1.02382.0250) and 2 U/ml of Liberase™ Research Grade (Roche, cat. no. 05401127001). PPs and incubation medium were transferred into a 15 ml conical tube and washed with 12 ml DMEM. After centrifugation at 400 g for 4 minutes at 4° C., supernatant was discarded and pellet was resuspended in 500 µl of ice-cold DMEM and transferred on a 70 µm cell strainer (Becton Dickinson, cat. no. 352350) previously placed over a 50 ml conical tube. Tissues were crushed over the Cell strainer using a syringe piston (black part). Cell strainer and piston were rinsed with 10 ml of ice-cold DMEM. Cell suspension was then passed through a 40 µm Cell strainer (Becton Dickinson, cat. no. 352340) previously placed on another 50 ml conical tube. Cell strainer was again rinsed with 5 ml of ice-cold DMEM. Cell suspension was transferred in a 15 ml conical tube and centrifuged at 400 g for 5 minutes at 4° C. Supernatant was discarded and pellet of isolated cells was resuspended in 1 ml of ice-cold DMEM—10% FCS as above. Cell counts and viability (typically >80%) was measured with trypan blue staining by microscopy approach. Cells were kept at 4° C. until further use.

In order to isolate white blood cells, blood samples were centrifuged at 700 g during 10 minutes at 4° C. Supernatant (plasma) was discarded and pellet was resuspended in 1 ml of red blood cell lysis buffer ($NH_4Cl$ 0.15M (Sigma, cat. no. A 9434), $KHCo_3$ 10 mM (Sigma Aldrich, cat. no. 431583) and EDTA 0.1 mM (Promega, cat. no. V4231)). Cell solution was then directly transferred in a 15 ml conical tube and incubated for one minute at room temperature. Lysis reaction was then stopped by filling the tube with DMEM—10% FCS medium and mixing. Cell suspension was centrifuged for five minutes at 400 g and supernatant was discarded. If cell pellet was still red, lysis step was repeated until pellet became white as mainly composed of white blood cells. Finally, cells were resuspended in DMEM—10% FCS, measured for counts and viability as for PPs cells above and kept at 4° C. until further use.

Measurement of the endogenous IgA production was used as recognized marker to monitor immune maturation (Macpherson A J, Mc Coy K D, Johansen F E, Brandtzaeg P.; *The immune geography of IgA induction and function*; Mucosal Immunol 2008; 1:11-22). In the present study, this was achieved using the IgA ELISPOT technique, allowing accurate counting of the number of IgA secreting cells in PPs and blood cell preparation. Wells of a 96-well cellulose multi-Screen-HA sterile plates (Millipore, cat. no. MAHA S45 10) were incubated 2 h at 37° C. (dry incubator) with 100 µl of a 1:200 dilution of a goat anti-mouse IgA (alpha-chain specific) antiserum (Sigma, cat. no. 8769) in sterile PBS. After washing of the wells 4 times with 200 µl/well of sterile PBS, wells were filled with 200 µl of RPMI-1640 culture medium (Invitrogen, cat. no. 61870-010) completed with 5% of inactivated fetal calf serum (FCS, Amimed 2-01F10-1) and incubated again 2 h at 37° C. in a humid cell culture incubator. PPs and blood cell suspensions prepared before were centrifuged (400 g for 5 minutes at 4° C.), supernatant was discarded and cell pellet was resuspended in 37° C. pre-heated RPMI-5% FCS medium at a concentration of 2×1E6 cells/ml. Wells of the 96-well plate were emptied and filled with 100 µl of the PPs and freshly prepared blood cell suspensions. Each cell suspension sample was tested as triplicates. Plate was then incubated for 18 hours at 37° C. in a humid cell culture incubator. After washing of the wells four times with 200µl/well of sterile PBS, wells were filled with 100 µl of a freshly prepared 1:500 dilution of a goat anti-mouse IgA (alpha-chain specific) antiserum conjugated to biotin (KPL, cat, no. 16-18-01) in PBS complemented with 0.05% Tween 20 (Bio-Rad, cat. no. 170-6531) and incubated for 1 h 30 at room temperature. After another washing of the wells four times with 200 µl/well of sterile PBS, wells were filled with 100 µl of a freshly prepared 1:500 dilution of a streptavidin-alkaline phosphatase (Sigma, cat. no. E-2636) in PBS-0.05% Tween 20 and incubated for 1 h at room temperature. After another washing step as above, wells were filled with 100 µl of a freshly prepared dissolution of one tablet of BCIP/NBT substrate (Sigma, cat. no. B-5655) in distilled water and incubated for 5 minutes at room temperature. Plate was then rinsed with distilled water. Plate's plastic bottom was then removed and allowed to dry at room temperature for at least 6 hours in dark conditions. Number of spots (1 spot=1 IgA secreting cell) for each well was then automatically counted using an AID ELISPOT reader system (Autoimmun Diagnostika GmbH) and were reported as number of IgA-secreting cells per 1E6 total cells.

Results from the IgA ELISPOT assays (shown on FIG. 8) revealed that supplementation of neonatal pups with infant formula containing the probiotic-SIgA pre-associated complexes (Group 5) achieved highest promotion of immune maturation among all tested groups. This was the case at both mucosal (PPs, FIG. 8A) and systemic (blood, FIG. 8B) levels. Pre-association of probiotics and SIgA according to the process of the present invention proved to be more efficient than probiotics and SIgA given together, but not in a pre-associated format (Group 4). Second, pre-association of probiotics and SIgA in infant formula provided a synergistic impact on endogenous IgA production when compared with the respective impacts of probiotics or SIgA added alone to infant formula matrix (Groups 2 and 3 respectively), using base infant formula as reference (Group 1).

These in vivo data confirm the value of the present industrial process for making a novel bioactive ingredient for infant formula.

The invention claimed is:

1. A method for production of a composition comprising secretory IgA and a probiotic, the method comprising the steps of:
   (a) providing a source of SIgA in the form of milk or a fraction thereof;
   (b) pasteurizing the milk at a temperature of 82-84° C. for a duration of 5-7 seconds(s); and
   (c) admixing with the probiotic, wherein the admixing is carried out at a temperature of 1-45° C. for a duration of 10-1440 minutes (min).

2. The method of claim 1, wherein the admixing of step (c) is carried out at a temperature of 36-38° C. for a duration of 28-32 min.

3. The method of claim 1, wherein the amount of secretory IgA per $2\times10^7$ CFU of the probiotic in the mixture of step (c) is 0.34 ng-20 µg.

4. The method of claim 1, wherein the concentration of the probiotic in the mixture of step (c) is $1\times10^6$-$1\times10^{11}$ CFU/mL.

5. The method of claim 1, wherein the milk provided in step (a) has not been exposed to a temperature of greater than 70° C., following expression.

6. The method of claim 1, wherein the probiotic is *Bifidobacterium lactis* or *Bifidobacterium longum* subspecies *infantis*.

7. The method of claim 1, wherein the secretory IgA and the probiotic are at least partially associated in the composition.

8. The method of claim 1, wherein the composition comprises 0.0001-10 mg secretory IgA per daily dose.

9. The method of claim 1, wherein the composition comprises between $1\times10^2$ and $1\times10^{12}$ cells of probiotics per daily dose.

* * * * *